US009255049B2

(12) United States Patent
Hori et al.

(10) Patent No.: US 9,255,049 B2
(45) Date of Patent: *Feb. 9, 2016

(54) RUTHENIUM COMPLEX AND METHOD FOR PREPARING OPTICALLY ACTIVE ALCOHOL COMPOUNDS USING THE SAME AS A CATALYST

(75) Inventors: Kiyoto Hori, Kanagawa (JP); Kazuhiko Matsumura, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/009,687

(22) PCT Filed: Apr. 2, 2012

(86) PCT No.: PCT/JP2012/002265
§ 371 (c)(1),
(2), (4) Date: Mar. 12, 2014

(87) PCT Pub. No.: WO2012/137460
PCT Pub. Date: Oct. 11, 2012

(65) Prior Publication Data
US 2014/0187809 A1    Jul. 3, 2014

(30) Foreign Application Priority Data
Apr. 6, 2011 (JP) .................... 2011-084879

(51) Int. Cl.
*C07F 9/50* (2006.01)
*C07C 29/145* (2006.01)
*B01J 31/18* (2006.01)
*B01J 31/24* (2006.01)
*C07F 15/00* (2006.01)
*C07F 9/655* (2006.01)

(52) U.S. Cl.
CPC .......... *C07C 29/145* (2013.01); *B01J 31/1805* (2013.01); *B01J 31/2452* (2013.01); *C07F 9/5027* (2013.01); *C07F 9/65517* (2013.01); *C07F 15/0046* (2013.01); *C07F 15/0053* (2013.01); *B01J 2231/643* (2013.01); *B01J 2531/0238* (2013.01); *B01J 2531/0266* (2013.01); *B01J 2531/821* (2013.01); *C07B 2200/07* (2013.01)

(58) Field of Classification Search
USPC ......................... 556/13, 16, 19, 22
See application file for complete search history.

(56) References Cited

U.S. PATENT DOCUMENTS

2013/0041151 A1* 2/2013 Nara et al. ................ 546/4

FOREIGN PATENT DOCUMENTS

| JP | 11-189600 A | 7/1999 |
| JP | 2003104993 A | 4/2003 |
| JP | 2004238306 A | 8/2004 |
| JP | 2011246435 A | 12/2011 |
| WO | 2005016943 A1 | 2/2005 |
| WO | 2007005550 A1 | 1/2007 |
| WO | 2009007443 A2 | 1/2009 |
| WO | 2009055912 A1 | 5/2009 |
| WO | 2011/135753 A1 | 11/2011 |

OTHER PUBLICATIONS

International Preliminary Report on Patentability from the International Bureau issued in connection with corresponding International Application No. PCT/JP2012/002265 issued on Nov. 5, 2013.
Matsumura, Kazuhiko, et al., "Chiral Ruthenabicyclic Complexes: Precatalysts for Rapid, Enantioselective, and Wide-Scope Hydrogenation of Ketones", ACS Publications, 2011, 133, 10696-10699.
Extended European Search Report for corresponding European Application Serial No. 12767831.6, Aug. 4, 2014, 5 pages.

* cited by examiner

*Primary Examiner* — Sudhakar Katakam
*Assistant Examiner* — Pancham Bakshi
(74) *Attorney, Agent, or Firm* — Mintz Levin Cohn Ferris Glovsky and Popeo, P.C.; Peter F. Corless; Christopher R. Crowles

(57) ABSTRACT

The present invention provides a novel ruthenium complex which has an excellent catalytic activity in terms of reactivity for an asymmetric reduction of a carbonyl compound and enantioselectivity, a catalyst using the ruthenium complex, and a method for preparing optically active alcohol compounds using the ruthenium complex. The present invention relates to a ruthenium complex having a ruthenacycle structure, a catalyst for an asymmetric reduction consisting of the ruthenium complex, and a method for preparing optically active alcohol compounds using the ruthenium complex.

16 Claims, No Drawings

RUTHENIUM COMPLEX AND METHOD FOR PREPARING OPTICALLY ACTIVE ALCOHOL COMPOUNDS USING THE SAME AS A CATALYST

CROSS-REFERENCES TO RELATED APPLICATIONS

This application is a 35 U.S.C. §371 U.S. national entry of International Application PCT/JP2012/002265 (WO 2012/137460) having an International filing date of Apr. 2, 2012, which claims under 35 U.S.C. §119(a) the benefit of Japanese Application No. 2011-084879, filed Apr. 6, 2011, the entire contents of which are incorporated herein by reference.

TECHNICAL FIELD

The present invention relates to a novel ruthenium complex and a method for preparing optically active alcohol compounds using the same as a catalyst.

BACKGROUND ART

A transition metal complex which has an optically active diphosphine compound as a ligand is very useful as a catalyst for an asymmetric reaction, and until now many catalysts have been developed.

Among the catalysts, in combination of a base compound, a ruthenium-diphosphine-diamine complex is known as a highly active catalyst for an asymmetric hydrogenation (for example, Patent Literature 1). As a method for synthesizing the complex, [RuCl$_2$(p-cymene)]$_2$ as a precursor of the complex reacted with an optically active diphosphine and an optically active diamine in order in a specific solvent is known (Patent Literature 2), as an example. In addition, as a complex having an optically active diphosphine and a tridentate amine ligand, the compound represented by the following formula is known (Patent Literature 3).

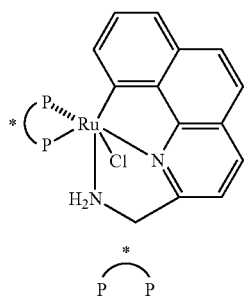

(R,S)-JOSIPHOS
(S,S)-SKEWPHOS
(S)—MeO-BIPHEP

A ruthenium-diphosphine-diamine complex having a counter anion is also known (Patent Literature 4).

The ruthenium metal complex having an optically active diphosphine compound and a diamine compound as a ligand is highly useful because of the use for an asymmetric hydrogenation of various carbonyl compounds, showing a high activity and a high enantioselectivity, and giving an optically active alcohol compound with high optical purity. However, such catalyst shows a high performance but not for every carbonyl compound, then the development of a catalyst with higher activity is needed.

PRIOR ART DOCUMENTS

Patent Literature

Patent Literature 1: JP 11-189600 A
Patent Literature 2: WO 2007/005550 A1
Patent Literature 3: WO 2009/007443 A2
Patent literature 4: WO 2009/055912 A1

SUMMARY OF THE INVENTION

Problems to be Solved by the Invention

The present invention provides a novel ruthenium metal complex having an excellent catalytic activity with an optically active diphosphine compound and a diamine compound as a ligand, and an asymmetric reduction catalyst using the metal complex, and a method for asymmetric reduction of a carbonyl compound using the metal complex.

Means for Solving the Problems

Inventors of the present invention intensively studied to solve the problems described above, and as a result, found a novel ruthenium complex having an optically active diphosphine and a tridentate diamine as a ligand which was used for an asymmetric reduction, and also developed a method for obtaining an optically active alcohol with high selectivity and higher activity than the catalysts of conventional technologies by using the complex as a catalyst.

Specifically, the present invention provides a novel ruthenium complex, an asymmetric reduction catalyst which includes the metal complex, and a method for preparing optically active alcohols according to an asymmetric reduction by using the metal complex.

The present invention provides the following [1] to [21].

[1] A ruthenium complex represented by the following Formula (1)

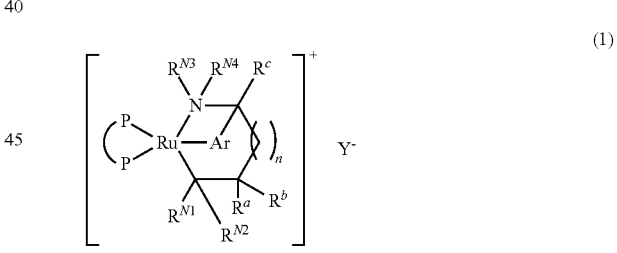

(in the formula,

represents a diphosphine and Y$^-$ represents a counter anion; R$^a$, R$^b$ and R$^c$ each independently represent a hydrogen atom, an optionally substituted C$_1$-C$_{20}$ alkyl group, an optionally substituted C$_2$-C$_{20}$ alkenyl group, an optionally substituted C$_3$-C$_8$ cycloalkyl group, an optionally substituted C$_7$-C$_{20}$ aralkyl group, an optionally substituted aryl group, or an optionally substituted heterocyclic group, and R$^b$ and R$^c$ may form an alkylene group or an alkylenedioxy group; R$^{N1}$, R$^{N2}$, R$^{N3}$, and R$^{N4}$ each independently represent a hydrogen atom, an optionally substituted C$_1$-C$_{20}$ alkyl group, an optionally substituted C$_2$-C$_{20}$ alkenyl group, an optionally substituted $C_7$-$C_{20}$ aralkyl group, or an optionally substituted $C_3$-$C_8$ cycloalkyl group, at least one of $R^{N1}$, $R^{N2}$, $R^{N3}$, and $R^{N4}$ represents a hydrogen atom, and $R^{N1}$ and $R^a$ may form an alkylene group; n represents an integer of 0 to 3; and Ar represents an optionally substituted arylene group).

[2] The ruthenium complex according to the above [1], wherein the ruthenium complex is a ruthenium complex represented by the following Formula (2)

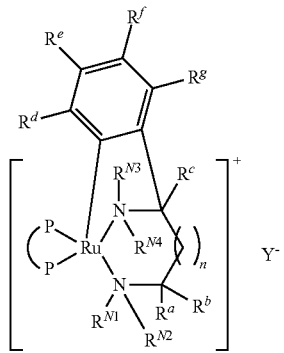

(2)

(in the formula,

represents diphosphine, $Y^-$ represents a counter anion; $R^a$, $R^b$, and $R^c$ each independently represent a hydrogen atom, an optionally substituted $C_1$-$C_{20}$ alkyl group, an optionally substituted $C_2$-$C_{20}$ alkenyl group, an optionally substituted $C_3$-$C_8$ cycloalkyl group, an optionally substituted $C_7$-$C_{20}$ aralkyl group, an optionally substituted aryl group, or an optionally substituted heterocyclic group, and $R^b$ and $R^c$ may form an alkylene group or an alkylenedioxy group; $R^d$, $R^e$, $R^f$ and $R^g$ each independently represent a hydrogen atom, an alkyl group having 1 to 20 carbon atoms, a halogenated alkyl group having 1 to 5 carbon atoms, a halogen atom, an optionally substituted aryl group, an optionally substituted $C_3$-$C_8$ cycloalkyl group, a tri-substituted silyl group or an alkoxy group having 1 to 20 carbon atoms; $R^{N1}$, $R^{N2}$, $R^{N3}$ and $R^{N4}$ each independently represent a hydrogen atom, an optionally substituted $C_1$-$C_{20}$ alkyl group, an optionally substituted $C_2$-$C_{20}$ alkenyl group, an optionally substituted $C_7$-$C_{20}$ aralkyl group, or an optionally substituted $C_3$-$C_8$ cycloalkyl group, and at least one of $R^{N1}$, $R^{N2}$, $R^{N3}$ and $R^{N4}$ represents a hydrogen atom; and $R^{N1}$ and $R^a$ may form an alkylene group).

[3] The ruthenium complex according to the above [1] or [2], wherein the ruthenium complex is a ruthenium complex represented by the following Formula (3)

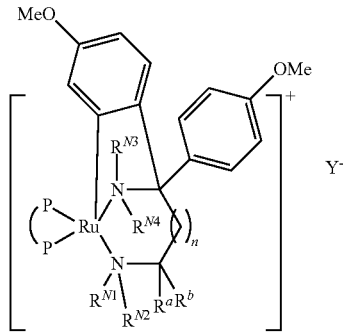

(3)

(in the formula,

represents diphosphine, $Y^-$ represents a counter anion, $R^a$ and $R^b$ each independently represent a hydrogen atom, an optionally substituted $C_1$-$C_{20}$ alkyl group, an optionally substituted $C_2$-$C_{20}$ alkenyl group, an optionally substituted $C_3$-$C_8$ cycloalkyl group, an optionally substituted $C_7$-$C_{20}$ aralkyl group, an optionally substituted aryl group, or an optionally substituted heterocyclic group; $R^{N1}$, $R^{N2}$, $R^{N3}$ and $R^{N4}$ each independently represent a hydrogen atom, an optionally substituted $C_1$-$C_{20}$ alkyl group, an optionally substituted $C_2$-$C_{20}$ alkenyl group, an optionally substituted $C_7$-$C_{20}$ aralkyl group, or an optionally substituted $C_3$-$C_8$ cycloalkyl group, and at least one of $R^{N1}$, $R^{N2}$, $R^{N3}$ and $R^{N4}$ represents a hydrogen atom; and $R^{N1}$ and $R^a$ may form an alkylene group).

[4] The ruthenium complex according to any one of the above [1] to [3], wherein the diphosphine indicated as

is a diphosphine represented by the following Formula (4)

$$R^1R^2P-Q-PR^3R^4 \qquad (4)$$

(in the formula, $R^1$, $R^2$, $R^3$ and $R^4$ each independently represent an optionally substituted aryl group, an optionally substituted cycloalkyl group, or an optionally substituted alkyl group, and $R^1$ and $R^2$ and/or $R^3$ and $R^4$ may form a ring; and Q represents an optionally substituted a divalent arylene group, a biphenyldiyl group, a binaphthalenediyl group, a bipyridinediyl group, a paracyclophanediyl group or a ferrocenediyl group).

[5] The ruthenium complex according to any one of the above [1] to [4], wherein the diphosphine indicated as

is an optically active diphosphine.

[6] The ruthenium complex according to any one of the above [1] to [5], wherein the optically active diphosphine indicated as

is a diphosphine represented by the following Formula (5)

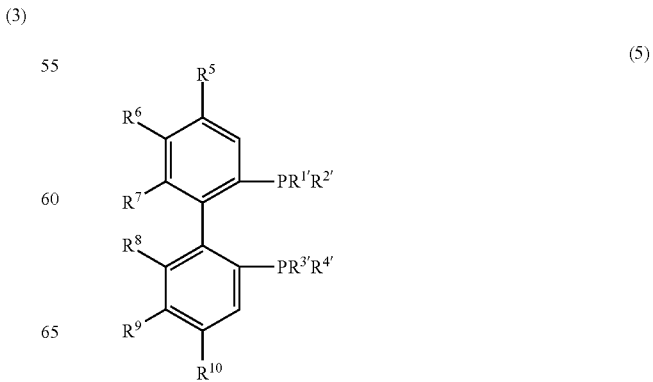

(5)

(in the formula, $R^{1'}$, $R^{2'}$, $R^{3'}$ and $R^{4'}$ each independently represent a phenyl group, a cyclopentyl group or a cyclohexyl group, and any of which is optionally substituted with a substituent group selected from a group consisting of an alkyl group having 1 to 4 carbon atoms and an alkoxy group having 1 to 4 carbon atoms. $R^5$, $R^6$, $R^7$, $R^8$, $R^9$ and $R^{10}$ each independently represent a hydrogen atom, an alkyl group having 1 to 4 carbon atoms, an alkoxy group having 1 to 4 carbon atoms, a halogen atom, a halogenated alkyl group or a dialkylamino group having 1 to 4 carbon atoms and two of $R^5$, $R^6$ and $R^7$ may form an optionally substituted alkylene group; an optionally substituted alkylenedioxy group; or an optionally substituted aromatic ring, two of $R^8$, $R^9$ and $R^{10}$ may form an optionally substituted alkylene group; an optionally substituted alkylenedioxy group; or an optionally substituted aromatic ring; and $R^7$ and $R^8$ may form an optionally substituted alkylene group; an optionally substituted alkylenedioxy group; or an optionally substituted aromatic ring, with the proviso that any of $R^7$ and $R^8$ is not a hydrogen atom).

[7] The ruthenium complex according to the above [6], wherein $R^1$, $R^2$, $R^3$ and $R^4$ in the Formula (4) and $R^{1'}$, $R^{2'}$, $R^{3'}$ and $R^{4'}$ in the Formula (5) is a 3,5-xylyl group.

[8] An asymmetric reduction catalyst comprising the ruthenium complex according to any one of the above [5] to [7].

[9] A method for preparing optically active alcohols, wherein a carbonyl group is subjected to an asymmetric hydrogenation with the asymmetric reduction catalyst according to the above [8] in the presence of a base compound.

[10] A method for preparing optically active alcohols, wherein a carbonyl group is subjected to an asymmetric hydrogen-transfer reduction with the asymmetric reduction catalyst according to the above [8] in the presence of a base compound.

[11] A method for preparing the ruthenium complex represented by the following Formula (1),

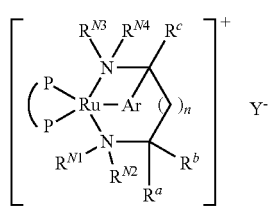

(1)

wherein the ruthenium compound represented by the following Formula (A)

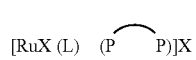

(A)

[RuX (L) (P⌒P)]X (in the formula, Ru represents a ruthenium atom, X represents a halogen atom, L represents an arene and

P⌒P represents a diphosphine)
is reacted with the compound having the following Formula (8)

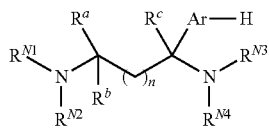

(8)

(in the formula, $R^a$, $R^b$ and $R^c$ each independently represent a hydrogen atom, an optionally substituted $C_1$-$C_{20}$ alkyl group, an optionally substituted $C_2$-$C_{20}$ alkenyl group, an optionally substituted $C_3$-$C_8$ cycloalkyl group, an optionally substituted $C_7$-$C_{20}$ aralkyl group, an optionally substituted aryl group or an optionally substituted heterocyclic group; or $R^b$ and $R^c$ may form an alkylene group or an alkylenedioxy group; $R^{N1}$, $R^{N2}$, $R^{N3}$ and $R^{N4}$ each independently represent a hydrogen atom, an optionally substituted $C_1$-$C_{20}$ alkyl group, an optionally substituted $C_2$-$C_{20}$ alkenyl group, an optionally substituted $C_7$-$C_{20}$ aralkyl group, or an optionally substituted $C_3$-$C_8$ cycloalkyl group, and at least one of $R^{N1}$, $R^{N2}$, $R^{N3}$ and $R^{N4}$ represents a hydrogen atom; or $R^{N1}$ and $R^a$ may form an alkylene group, and n is an integer of 0 to 3, and Ar represents an optionally substituted arylene group); then to react with a metal salt having a counter anion $Y^-$.

[12] A method for preparing the ruthenium complex represented by the following Formula (1),

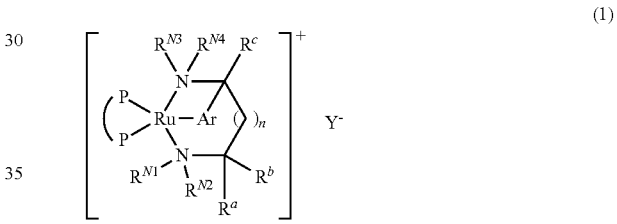

(1)

wherein the ruthenium compound represented by the following Formula (B)

$[RuX_2(L)]_m$ (B)

(in the formula, Ru represents a ruthenium atom, X represents a halogen atom, L represents an arene and m represents a natural number of 2 or more)
is reacted with a diphosphine represented as

P⌒P and then with the compound having the following Formula (8)

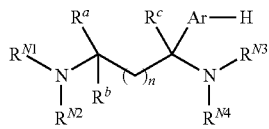

(8)

(in the formula, $R^a$, $R^b$ and $R^c$ each independently represent a hydrogen atom, an optionally substituted $C_1$-$C_{20}$ alkyl group, an optionally substituted $C_2$-$C_{20}$ alkenyl group, an optionally substituted $C_3$-$C_8$ cycloalkyl group, an optionally substituted $C_7$-$C_{20}$ aralkyl group, an optionally substituted aryl group or an optionally substituted heterocyclic group; or $R^b$ and $R^c$ may form an alkylene group or an alkylenedioxy group; $R^{N1}$, $R^{N2}$, $R^{N3}$ and $R^{N4}$ each independently represent a hydrogen atom, an optionally substituted $C_1$-$C_{20}$ alkyl group, an optionally substituted $C_2$-$C_{20}$ alkenyl group, an optionally substituted $C_7$-$C_{20}$ aralkyl group, or an optionally substituted $C_3$-$C_8$ cycloalkyl group, and at least one of $R^{N1}$, $R^{N2}$, $R^{N3}$ and $R^{N4}$ represents a hydrogen atom; or $R^{N1}$ and $R^a$ may be an alkylene group, and n is an integer of 0 to 3 and Ar represents an optionally substituted arylene group); further to react with a metal salt having a counter anion $Y^-$.

[13] The method for preparing the ruthenium complex according [11] or [12], wherein the reaction was carried out in presence of a solvent, and the solvent used is an alcohol solvent.

[14] The method for preparing the ruthenium complex according to any one of the above [11] to [13], additionally wherein a base is added.

[15] The method for preparing the ruthenium complex according to any one of the above [11] to [14], wherein the diphosphine indicated as

is a diphosphine represented by the following Formula (4)

$$R^1R^2P\text{-}Q\text{-}PR^3R^4 \quad (4)$$

(in the formula, $R^1$, $R^2$, $R^3$ and $R^4$ each independently represent an optionally substituted aryl group, an optionally substituted cycloalkyl group or an optionally substituted alkyl group, and $R^1$ and $R^2$ and/or $R^3$ and $R^4$ may form a ring; and Q represents an optionally substituted divalent arylene group, a biphenyldiyl group, a binaphthalenediyl group, a bipyridinediyl group, a paracyclophanediyl group or a ferrocenediyl group).

[16] The method for the preparing according to any one of the above [11] to [15], wherein the diphosphine indicated as

is an optically active diphosphine.

[17] The method for preparing the ruthenium complex according to any one of the above [11] to [16], wherein the optically active diphosphine indicated a

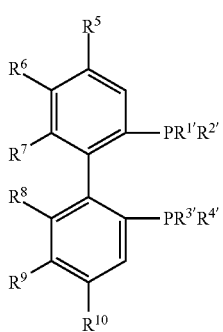

is an optically active diphosphine represented by the following Formula (5)

(in the formula, $R^{1'}$, $R^{2'}$, $R^{3'}$ and $R^{4'}$ each independently represent a phenyl group, a cyclopentyl group or a cyclohexyl group, and any of which is optionally substituted with a substituent group selected from a group consisting of an alkyl group having 1 to 4 carbon atoms and an alkoxy group having 1 to 4 carbon atoms.

$R^5$, $R^6$, $R^7$, $R^8$, $R^9$ and $R^{10}$ each independently represent a hydrogen atom, an alkyl group having 1 to 4 carbon atoms, an alkoxy group having 1 to 4 carbon atoms, a halogen atom, a halogenated alkyl group or a dialkylamino group having 1 to 4 carbon atoms, and two of $R^5$, $R^6$ and $R^7$ may form an optionally substituted alkylene group, an optionally substituted alkylenedioxy group or an optionally substituted aromatic ring, and two of $R^8$, $R^9$ and $R^{10}$ may form an optionally substituted alkylene group, an optionally substituted alkylenedioxy group or an optionally substituted aromatic ring; and $R^7$ and $R^8$ may form an optionally substituted alkylene group, an optionally substituted alkylenedioxy group or an optionally substituted aromatic ring, with the proviso that $R^7$ and $R^8$ are not a hydrogen atom).

[18] The method for the preparing the ruthenium complex according to any one of the above [11] to [16], wherein $R^1$, $R^2$, $R^3$ and $R^4$ in the Formula (4) and $R^{1'}$, $R^{2'}$, $R^{3'}$ and $R^{4'}$ in the Formula (5) is a 3,5-xylyl group.

[19] A method for preparing the ruthenium complex represented by the following Formula (1),

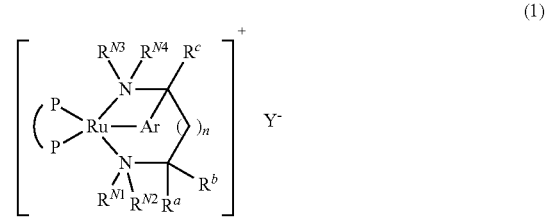

wherein the ruthenium compound represented by the following Formula (9)

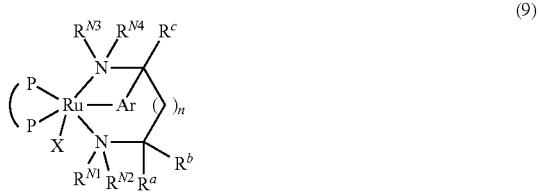

is reacted with a metal salt having a counter anion $Y^-$.

[20] The method according to [19], wherein the metal salt having the counter anion $Y^-$ is an alkali metal or a silver trifluoromethanesulfonate, an alkali metal or a silver borate, an alkali metal or a silver phosphate, an alkali metal or a silver antimonate, an alkali metal or a silver perchlorate or an alkali metal or a silver arsenate.

[21] The method according to [20], wherein an alkali metal or a silver borate is sodium tetrafluoroborate, silver tetrafluoroborate, sodium tetraphenylborate or silver tetraphenylborate; an alkali metal or a silver phosphate is sodium hexafluorophosphate or silver hexafluorophosphate; an alkali metal or a silver antimonate is sodium hexafluoroantimonate or silver hexafluoroantimonate; an alkali metal or a silver perchlorate is sodium perchlorate or silver perchlorate; or an alkali metal or a silver arsenate is sodium hexafluoroarsenate or silver hexafluoroarsenate.

Effects of the Invention

The present invention provides a novel ruthenium complex and a method for preparing an optically active alcohol compound using the complex as a catalyst. The novel ruthenium complex catalysts in the present invention shows good reactivity in an asymmetric reduction of a carbonyl compound, especially conversion rate and selectivity, also shows enantioselectivity, etc., compared to conventional optically active ruthenium complex catalysts having a diphosphine and a diamine ligand, and therefore it is industrially highly useful.

Moreover, as the ruthenium complex is expensive, it is preferable to minimize the amount of the ruthenium complex used for the reaction. In this regard, according to the invention, a complex having high catalytic activity which requires less amount of a catalyst for reaction than conventional asymmetric reduction complex is provided.

MODES FOR CARRYING OUT THE INVENTION

Hereinafter, the present invention will be explained in detail.

The ruthenium complex represented by the Formula (1) of the invention is characterized in that a divalent arylene group represented by —Ar— is included therein, and it is specifically characterized in that one end of the arylene group binds to the ruthenium atom with Ru-carbon bond and the other end binds to the carbon atom in the carbon chain of a diamine compound as a ligand with a carbon-carbon bond. It is further characterized in that any of the two nitrogen atoms in the diamine compound as a ligand has $sp^3$ hybridization. Moreover, the arylene group may have a substituent group such as an alkoxy group.

One of the characteristics of the ruthenium complex of the invention is that it is a ruthenium complex having a ruthenacycle structure.

Examples of the optionally substituted arylene group which is represented by Ar in the ruthenium complex of the Formula (1) of the invention include a divalent monocyclic, polycyclic or condensed-ring type arylene group having 6 to 36 carbon atoms, preferably 6 to 18 carbon atoms, and more preferably 6 to 12 carbon atoms, or a divalent monocyclic, polycyclic or condensed-ring type heteroarylene group having a 3- to 8-membered ring, and preferably 5- to 8-membered ring in which 1 to 4, preferably 1 to 3, or 1 or 2 heteroatoms consisting of a nitrogen atom, an oxygen atom and a sulfur atom is included. Examples of a preferred arylene group include a phenylene group, a naphthalenediyl group, a pyridinediyl group, a thiophenediyl group and a furandiyl group, and a phenylene group is particularly preferable. Although the position to which the divalent arylene group binds is not specifically limited, two adjacent carbon atom positions (i.e., ortho position) are preferable.

In addition, examples of a substitutent group which is substituted on the arylene group include a linear or branched alkyl group, a linear or branched alkoxy group, a cycloalkyl group, a halogen atom, an aryl group, a heteroaryl group, and a tri-substituted silyl group.

Hereinafter, the substituent group which is substituted on the arylene group will be explained.

Examples of the linear or branched alkyl group, may be substituted by halogen atom such as a fluorine atom, include a linear or branched alkyl group having 1 to 10 carbon atoms, preferably 1 to 6 carbon atoms, and more preferably 1 to 4 carbon atoms. Specific examples include a methyl group, an ethyl group, a n-propyl group, an isopropyl group, a n-butyl group, an isobutyl group, a sec-butyl group, a tert-butyl group and a trifluoromethyl group.

Examples of the linear or branched alkoxy group include a linear or branched alkoxy group having 1 to 10 carbon atoms, preferably 1 to 6 carbon atoms, and more preferably 1 to 4 carbon atoms. Specific examples include a methoxy group, an ethoxy group, a n-propoxy group, an isopropoxy group, a n-butoxy group, a sec-butoxy group, an isobutoxy group and a tert-butoxy group.

Examples of the cycloalkyl group include a saturated or unsaturated monocyclic, polycyclic or condensed-ring type cycloalkyl group having 3 to 15 carbon atoms, and preferably 5 to 7 carbon atoms, and specific examples include a cyclopentyl group and a cyclohexyl group. One or two or more alkyl groups having 1 to 4 carbon atoms or alkoxy groups having 1 to 4 carbon atoms may be substituted on the ring of these cycloalkyl groups.

Examples of the halogen atom include a chlorine atom, a bromine atom and a fluorine atom.

Examples of the aryl group include an aryl group having 6 to 14 carbon atoms, and specific examples include a phenyl group, a naphthyl group, an anthryl group, a phenanthryl group and a biphenyl group. The aryl group may have one or two or more substituent groups, and examples of the substituent group include an alkyl group having 1 to 4 carbon atoms and an alkoxy group having 1 to 4 carbon atoms as described above.

Examples of the heteroaryl group include a 5-membered or 6-membered cyclic group having an oxygen atom, a sulfur atom or a nitrogen atom, and specific examples include a furyl group, a thienyl group and a pyridyl group.

Examples of the tri-substituted silyl group include a silyl group which is tri-substituted with the alkyl group or the aryl group described above, and specific examples include a trimethylsilyl group, a triethylsilyl group, a triisopropylsilyl group, a tert-butyldimethylsilyl group, a diphenylmethylsilyl group and a dimethylphenylsilyl group.

Examples of the counter anion represented by $Y^-$ in the ruthenium complex of the Formulae (1), (2) and (3) include a complex anion such as $BF_4$, $BPh_4$, $BMe_4$, $BEt_4$, $BPr_4$, $BBu_4$, $PF_6$, $SbF_6$, $AsF_6$, $ClO_4$ and a trifluoromethanesulfonyloxy group (OTf).

The groups represented by $R^a$, $R^b$, $R^c$, $R^d$, $R^e$, $R^f$, $R^g$, $R^{N1}$, $R^{N2}$, $R^{N3}$ and $R^{N4}$ in the ruthenium complex of the Formulae (1), (2) and (3) will be explained hereinafter.

Examples of the $C_1$-$C_{20}$ alkyl group include a linear or branched alkyl group having 1 to 20 carbon atoms, preferably 1 to 5 carbon atoms and more preferably 1 to 4 carbon atoms, and specific examples include a methyl group, an ethyl group, a n-propyl group, an isopropyl group, a n-butyl group, an isobutyl group, a sec-butyl group, a tert-butyl group, a n-pentyl group, a n-hexyl group, a decyl group, a dodecyl group and a hexadecyl group.

Examples of the $C_2$-$C_{20}$ alkenyl group include a liner or branched alkenyl group having 2 to 20 carbon atoms, preferably 2 to 10 carbon atoms and more preferably 2 to 6 carbon atoms, and specific examples include an ethenyl group, a n-propenyl group, an isopropenyl group, a 1-butenyl group, a 1-buten-2-yl group, a pentenyl group and a hexenyl group.

Examples of the $C_1$-$C_{20}$ alkoxy group include an alkyl group having 1 to 20 carbon atoms to which an oxygen atom is bonded, and specific examples include a methoxy group, an ethoxy group, a n-propoxy group, an isopropoxy group, a n-butoxy group, a sec-butoxy group, an isobutoxy group and a tert-butoxy group.

The examples of halogenated $C_1$-$C_5$ alkyl group, include a trifluoromethyl group, a pentafluoroethyl group, a heptafluoropropyl group, a trichoromethyl group.

Examples of the $C_3$-$C_8$ cycloalkyl group include a saturated or unsaturated monocyclic, polycyclic or condensed-ring type cycloalkyl group having 3 to 8 carbon atoms, and preferably 5 to 7 carbon atoms. Specific examples include a cyclopentyl group and a cyclohexyl group.

Examples of the halogen atom include a chlorine atom, a bromine atom and a fluorine atom.

Examples of the heteroaryl group include a 5-membered or 6-membered cyclic group having an oxygen atom, a sulfur atom or a nitrogen atom, and specific examples include a furyl group, a thienyl group and a pyridyl group.

Examples of the tri-substituted silyl group include a silyl group which is tri-substituted with the alkyl group or the aryl group described above, and specific examples include a trimethylsilyl group, a triethylsilyl group, a triisopropylsilyl group, a tert-butyldimethylsilyl group, a diphenylmethylsilyl group and a dimethylphenylsilyl group.

Examples of the $C_7$-$C_{20}$ aralkyl group include an aralkyl group having 7 to 20 carbon atoms, preferably 7 to 15 carbon atoms and more preferably 7 to 10 carbon atoms in which an alkyl group having 1 to 20 carbon atoms is bonded to a monocyclic, polycyclic or condensed-ring type aryl group having 6 to 19 carbon atoms and preferably 6 to 14 carbon atoms. Specific examples include a benzyl group, an α-methylbenzyl group, an α,α-dimethylbenzyl group, a 2-phenylethyl group and a 3-phenylpropyl group.

Otherwise, the examples of the substituent to $C_1$-$C_{20}$ alkyl group, $C_2$-$C_{20}$ alkenyl group, $C_1$-$C_{20}$ alkoxy group, halogenated $C_1$-$C_5$ alkyl group, $C_3$-$C_8$ cycloalkyl group, heteroaryl group, tri-substituted silyl group and $C_7$-$C_{20}$ aralkyl group as described above include a linear or branched alkyl group, a linear or branched alkoxy group, a cycloalkyl group, a halogen atom, an aryl group, a heteroaryl group and a tri-substituted silyl group.

Examples of an aryl group in the optionally substituted aryl group include a monocyclic, polycyclic and condensed-ring type aryl group having 6 to 20 carbon atoms, preferably 6 to 14 carbon atoms, and more preferably 6 to 12 carbon atoms. Specific examples include a phenyl group, a naphthyl group, an anthryl group, a phenanthryl group and a biphenyl group, and a phenyl group is preferable. The aryl group may have one or two or more substituent groups, and examples of the substituent group include an alkyl group having 1 to 4 carbon atoms such as a methyl group, an isopropyl group and a tert-butyl group, and an alkoxy group having 1 to 4 carbon atoms such as a methoxy group, an ethoxy group, a n-propoxy group, an isopropoxy group, a n-butoxy group, an isobutoxy group, a sec-butoxy group and a tert-butoxy group as described above.

The examples of an optionally substituted heterocyclic group include a 5-membered or 6-membered cyclic group having an oxygen atom, a sulfur atom or a nitrogen atom, and specific examples include a furyl group, a thienyl group and a pyridyl group. And the examples of the substituent which the heterocyclic group has one or more than two of, include an alkyl group having 1 to 4 carbon atoms such as a methyl group, an isopropyl group and a tert-butyl group; alkoxy group having 1 to 4 carbon atoms such as a methoxy group, an ethoxy group, a n-propoxy group, an isopropoxy group, a n-butoxy group, a sec-butoxy group, an isobutoxy group and a tert-butoxy group.

Moreover, examples of the alkylene group formed by $R^b$ and $R^c$ include a linear or branched alkylene group having 1 to 6 carbon atoms and preferably 1 to 4 carbon atoms. Specific examples include a methylene group, an ethylene group, a trimethylene group, a propylene group and a tetramethylene group, and these alkylene groups are optionally substituted with an alkyl group having 1 to 4 carbon atoms or an alkoxy group having 1 to 4 carbon atoms.

Examples of the alkylenedioxy group formed by $R^b$ and $R^c$ include a linear or branched alkylenedioxy group having 1 to 6 carbon atoms and preferably 1 to 4 carbon atoms. Specific examples include a methylenedioxy group, an ethylenedioxy group and a trimethylenedioxy group.

The examples of the alkylene group formed by $R^{N1}$ and $R^a$ include a linear or branched alkylene group having 1 to 6 carbon atoms and preferably 1 to 4 carbon atoms. Specific examples include a methylene group, an ethylene group, a trimethylene group, a propylene group and a tetramethylene group, and these alkylene groups are optionally substituted with an alkyl group having 1 to 4 carbon atoms or an alkoxy group having 1 to 4 carbon atoms.

The diphosphine (also as named bisphosphine) represented by P∩P in the ruthenium complex of the Formulae (1), (2) and (3) is not specifically limited if it is a diphosphine which can coordinate to a ruthenium metal. Examples thereof include those represented by the following Formula (4)

$$R^1R^2P\text{-}Q\text{-}PR^3R^4 \qquad (4)$$

(in the formula, $R^1$, $R^2$, $R^3$ and $R^4$ each independently represent an optionally substituted aryl group, an optionally substituted cycloalkyl group or an optionally substituted alkyl group, and $R^1$ and $R^2$ and/or $R^3$ and $R^4$ may form a ring. Q represents an optionally substituted divalent arylene group, a biphenyldiyl group, a binaphthalenediyl group, a bipyridinediyl group, a paracyclophanediyl group or a ferrocenediyl group.).

Examples of the optionally substituted aryl group represented by $R^1$, $R^2$, $R^3$ and $R^4$ in the above formula include an aryl group having 6 to 14 carbon atoms, and specific examples include a phenyl group, a naphthyl group, an anthryl group, a phenanthryl group and a biphenyl group.

These aryl groups may have one or two or more substituent groups and the examples of the substituent group include an alkyl group and an alkoxy group.

Examples of the alkyl group as a substituent group for the aryl group include a linear or branched alkyl group having 1 to 15 carbon atoms, preferably 1 to 10 carbon atoms and more preferably 1 to 6 carbon atoms, and specific examples include a methyl group, an ethyl group, a n-propyl group, an isopropyl group, a n-butyl group, a sec-butyl group, an isobutyl group and a tert-butyl group.

Examples of the alkoxy group as a substituent group for the aryl group include a linear or branched alkoxy group having 1 to 6 carbon atoms, and the specific examples include a methoxy group, an ethoxy group, a n-propoxy group, an isopropoxy group, a n-butoxy group, a sec-butoxy group, an isobutoxy group and a tert-butoxy group.

Moreover, examples of the optionally substituted cycloalkyl group represented by $R^1$, $R^2$, $R^3$ and $R^4$ include a 5-membered or 6-membered cycloalkyl group, and preferred examples of the cycloalkyl group include a cyclopentyl group and a cyclohexyl group. On the ring of these cycloalkyl groups, one or two or more substituent groups such as an alkyl group or an alkoxy group, which is mentioned above as a substituent group for the aryl group, may be substituted.

Examples of the optionally substituted alkyl group include a linear or branched alkyl group having 1 to 15 carbon atoms, preferably 1 to 10 carbon atoms and more preferably 1 to 6 carbon atoms, and specific examples include a methyl group, an ethyl group, a n-propyl group, an isopropyl group, a n-butyl group, a sec-butyl group, an isobutyl group and a tert-butyl group. These alkyl groups are optionally substituted with one or two or more substituent groups such as an alkoxy group which is mentioned as a substituent group for the aryl group in the above.

Moreover, examples of the ring which may be formed by $R^1$ and $R^2$ and/or $R^3$ and $R^4$ include a ring which includes a phosphorus atom to which $R^1$, $R^2$, $R^3$ and $R^4$ are bonded, including a 4-membered, 5-membered or 6-membered ring. Specific examples include a phosphetane ring, a phospholane ring, a phosphane ring, a 2,4-dimethyl phosphetane ring, a 2,4-diethyl phosphetane ring, a 2,5-dimethyl phospholane ring, a 2,5-diethyl phospholane ring, a 2,6-dimethyl phosphane ring and a 2,6-diethyl phosphane ring, and these ring compounds may be optically active.

Moreover, examples of Q include an optionally substituted divalent arylene group, a biphenyldiyl group, a binaphthalenediyl group, a bipyridinediyl group, a paracyclophanediyl group and a ferrocenediyl group.

Examples of the divalent arylene group include a divalent arylene group which is derived from the aryl group described above. Preferred examples of the arylene group include a phenylene group. Examples of the phenylene group include an o- or m-phenylene group, and the phenylene group is optionally substituted with an alkyl group having 1 to 6 carbon atoms such as a methyl group, an ethyl group, a n-propyl group, an isopropyl group, a n-butyl group, a sec-butyl group, an isobutyl group and a tert-butyl group, an alkoxy group having 1 to 6 carbon atoms such as a methoxy group, an ethoxy group, a n-propoxy group, an isopropoxy group, a n-butoxy group, a sec-butoxy group, an isobutoxy group and a tert-butoxy group, a hydroxy group, an amino group or a substituted amino group.

The biphenyldiyl group, binaphthalenediyl group and bipyridinediyl group preferably have a 1,1'-biaryl-2,2'-diyl type structure in which an axial asymmetric structure is included, and the biphenyldiyl group, the binaphthalenediyl group and the bipyridinediyl group are optionally substituted with the alkyl group and the alkoxy group described above, for example, an alkylenedioxy group such as a methylenedioxy group, an ethylenedioxy group, a trimethylenedioxy group, a hydroxy group, an amino group and a substituted amino group.

Paracyclophanediyl group may be optionally substituted with the alkyl group and the alkoxy group described above, for example, an alkylenedioxy group such as a methylenedioxy group, an ethylenedioxy group and a trimethylenedioxy group, a hydroxy group, an amino group, and a substituted amino group.

Moreover, the ferrocenediyl group is also optionally substituted and examples of the substituent group include an alkyl group, an alkoxy group, an alkylenedioxy group, a hydroxy group, an amino group and a substituted amino group as described above.

Examples of the substituted amino group include an amino group which is substituted with one or two alkyl groups having 1 to 6 carbon atoms.

Specific examples of the diphosphine represented by the Formula (4) include an optically active diphosphine that are well known in the art, and preferred examples include the compound represented by the following Formula (5).

The optically active disphosphine represented by the following formula can be mentioned.

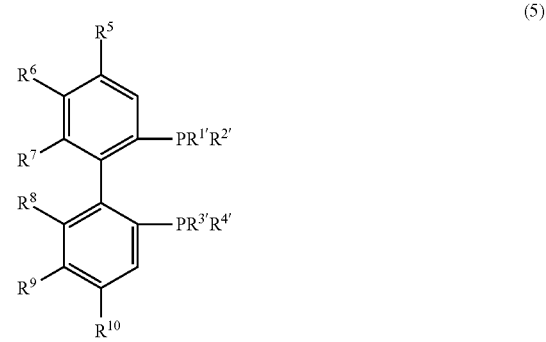

(5)

(in the formula, $R^{1'}$, $R^{2'}$, $R^{3'}$ and $R^{4'}$ each independently represent a phenyl group, a cyclopentyl group or a cyclohexyl group, and any of which is optionally substituted with a substituent group selected from a group consisting of an alkyl group having 1 to 4 carbon atoms and an alkoxy group having 1 to 4 carbon atoms. $R^5$, $R^6$, $R^7$, $R^8$, $R^9$ and $R^{10}$ each independently represent a hydrogen atom, an alkyl group having 1 to 4 carbon atoms, an alkoxy group having 1 to 4 carbon atoms, a halogen atom, a halogenated alkyl group or a dialkylamino group having 1 to 4 carbon atoms, two of $R^5$, $R^6$ and $R^7$ may form an optionally substituted alkylene group, an optionally substituted alkylenedioxy group; or an optionally substituted aromatic ring, and two of $R^8$, $R^9$ and $R^{10}$ may form an optionally substituted alkylene group; an optionally substituted alkylenedioxy group or an optionally substituted aromatic ring. Furthermore, $R^7$ and $R^8$ may form an optionally substituted alkylene group, an optionally substituted alkylenedioxy group or an optionally substituted aromatic ring, with the proviso that $R^7$ and $R^8$ are not a hydrogen atom.)

Regarding the alkyl group, the alkoxy group, the halogen atom, the alkylene group and the alkylenedioxy group in the above Formula (5), those described in the above can be mentioned. The aromatic ring which is formed by two groups may form a 6-membered aromatic ring together with adjacent atom. The aromatic ring thus formed is optionally substituted with alkyl groups or alkoxy groups.

Preferred examples of the Formula (5) include cases in which $R^{1'}$, $R^{2'}$, $R^{3'}$ and $R^{4'}$ each independently represent a phenyl group which is optionally substituted singular or plural number with a substituent group selected from a group consisting of an alkyl group having 1 to 4 carbon atoms and an alkoxy group having 1 to 4 carbon atoms, and $R^6$ and $R^7$ forms a tetramethylene group; a methylenedioxy group which is optionally substituted with alkyl groups having 1 to 4 carbon atoms or a fluorine atom; or forms a benzene ring together with an adjacent carbon atom; and $R^8$ and $R^9$ forms a tetramethylene group; a methylenedioxy group which is optionally substituted with an alkyl group having 1 to 4 carbon atoms or a fluorine atom; or forms a benzene ring together with an adjacent carbon atom.

Moreover, specific examples of more preferable optically active diphosphine of the invention include the optically active diphosphine represented by the following Formula (6) or Formula (7).

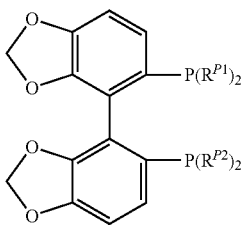

(6)

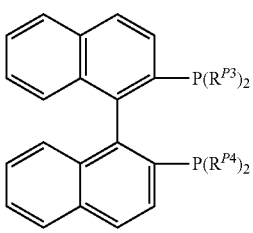

(7)

Specific examples of $R^{P1}$ and $R^{P2}$ in the Formula (6) and the specific examples of $R^{P3}$ and $R^{P4}$ in the Formula (7) include a phenyl group, a p-tolyl group, a m-tolyl group, an o-tolyl group, a 3,5-xylyl group, a 3,5-di-tert-butylphenyl group, a p-tert-butylphenyl group, a p-methoxyphenyl group, a 3,5-di-tert-butyl-4-methoxyphenyl group, a p-chlorophenyl group, a m-chlorophenyl group, a p-fluorophenyl group and a m-fluorophenyl group.

Specific examples of the diphosphine represented by the Formula (4), (5), (6) and (7) of the invention include 2,2'-bis(diphenylphosphino)-1,1'-binaphthyl(binap), 2,2'-bis[di(p-tolyl)phosphino]-1,1'-binaphthyl (tolbinap), 2,2'-bis[di(m-tolyl)phosphino]-1,1'-binaphthyl, 2,2'-bis[di(3,5-xylyl)phosphino]-1,1'-binaphthyl (xylbinap), 2,2'-bis[di(p-tert-butylphenyl)phosphino]-1,1'-binaphthyl, 2,2'-bis[di(p-methoxyphenyl)phosphino]-1,1'-binaphthyl, 2,2'-bis[di(3,5-di-tert-butyl-4-methoxyphenyl)phosphino]-1,1'-binaphthyl, 2,2'-bis[di(cyclopentyl)phosphino]-1,1'-binaphthyl, 2,2'-bis[di(cyclohexyl)phosphino]-1,1'-binaphthyl, 2,2'-bis(diphenylphosphino)-5,5',6,6',7,7',8,8'-octahydro-1,1'-binaphthyl, 2,2'-bis(di-p-tolylphosphino)-5,5',6,6',7,7',8,8'-octahydro-1,1'-binaphthyl, 2,2'-bis(di-m-tolylphosphino)-5,5',6,6',7,7',8,8'-octahydro-1,1'-binaphthyl, 2,2'-bis(di-3,5-xylylphosphino)-5,5',6,6',7,7',8,8'-octahydro-1,1'-binaphthyl (xylyl-H8-binap), 2,2'-bis(di-p-tert-butylphenylphosphino)-5,5',6,6',7,7',8,8'-octahydro-1,1'-binaphthyl, 2,2'-bis(di-p-methoxyphenylphosphino)-5,5',6,6',7,7',8,8'-octahydro-1,1'-binaphthyl, 2,2'-bis(di-p-chlorophenylphosphino)-5,5',6,6',7,7',8,8'-octahydro-1,1'-binaphthyl, 2,2'-bis(dicyclopentylphosphino)-5,5',6,6',7,7',8,8'-octahydro-1,1'-binaphthyl, 2,2'-bis(dicyclohexylphosphino)-5,5',6,6',7,7',8,8'-octahydro-1,1'-binaphthyl, ((4,4'-bi-1,3-benzodioxol)-5,5'-diyl)bis(diphenylphosphine) (segphos), (4,4'-bi-1,3-benzodioxol)-5,5'-diyl)bis(di(3,5-xylyl)phosphine) (dm-segphos), ((4,4'-bi-1,3-benzodioxol)-5,5'-diyl)bis(di(3,5-di-tert-butyl-4-methoxyphenyl)phosphine), ((4,4'-bi-1,3-benzodioxol)-5,5'-diyl)bis(di(4-methoxyphenyl)phosphine), ((4,4'-bi-1,3-benzodioxol)-5,5'-diyl)bis(dicyclohexylphosphine), ((4,4'-bi-1,3-benzodioxol)-5,5'-diyl)bis(bis(3,5-di-tert-butylphenyl)phosphine), 2,2'-bis(di-3,5-xylylphosphino)-6,6'-dimethoxy-1,1'-biphenyl (xylyl-MeO-biphep), 2,2'-bis(diphenylphosphino)-6,6'-dimethyl-1,1-biphenyl, 2,2'-bis(di-p-tolylphosphino)-6,6'-dimethyl-1,1'-biphenyl, 2,2'-bis(di-o-tolylphosphino)-6,6'-dimethyl-1,1'-biphenyl, 2,2'-bis(di-m-fluorophenylphosphino)-6,6'-dimethyl-1,1'-biphenyl, 2,2'-bis(diphenylphosphino)-6,6'-dimethoxy-1,1'-biphenyl, 2,2'-bis(di-p-tolylphosphino)-6,6'-dimethoxy-1,1'-biphenyl, 2,2',6,6'-tetramethoxy-4,4'-bis(di-3,5-xylylphosphino)-3,3'-bipyridine (xylyl-p-phos), 2,2',6,6'-tetramethoxy-4,4'-bis(diphenylphosphino)-3,3'-bipyridine, 2,2',6,6'-tetramethoxy-4,4'-bis(di-p-tolylphosphino)-3,3'-bipyridine, 2,2',6,6'-tetramethoxy-4,4'-bis(di-o-tolylphosphino)-3,3'-bipyridine, 4,12-bis(di-3,5-xylylphosphino)-[2.2]-paracyclophane, 4,12-bis(diphenylphosphino)-[2.2]-paracyclophane, 4,12-bis(di-p-tolylphosphino)-[2.2]-paracyclophane, 4,12-bis(di-o-tolylphosphino)-[2.2]-paracyclophane, 1,1'-bis(2,4-diethylphosphotano)ferrocene, 1,13-bis(diphenylphosphino)-7,8-dihydro-6H-dibenzo[f,h][1,5]dioxonin, 1,13-bis(bis(3,5-dimethylphenyl)phosphino)-7,8-dihydro-6H-dibenzo[f,h][1,5]dioxonin (xylyl-C3-tune-phos), and 6,6'-bis(bis(3,5-dimethylphenyl)phosphino)-2,2',3,3'-tetrahydro-5,5'-bi-1,4-benzodioxin (xylyl-synphos).

In addition to those described above, examples of the bisphosphine compound which can be used for the invention include N,N-dimethyl-1-[1',2-bis(diphenylphosphino)ferrocenyl]ethyl amine, 2,3-bis(diphenylphosphino)butane, 1-cyclohexyl-1,2-bis(diphenylphosphino)ethane, 2,3-O-isopropylidene-2,3-dihydroxy-1,4-bis(diphenylphosphino)butane, 1,2-bis[(o-methoxyphenyl)phenylphosphino]ethane, 1,2-bis(2,5-dimethylphosphorano)ethane, N,N'-bis(diphenylphosphino)-N,N'-bis(1-phenylethyl)ethylene diamine, 1,2-bis(diphenylphosphino)propane, 2,4-bis(diphenylphosphino)pentane, cyclohexylanisylmethylphosphine, 2,3-bis(diphenylphosphino)-5-norbornene, 3,4-bis(diphenylphosphino)-1-benzylpyrrolidine, 1-[1',2-bis(diphenylphosphino)ferrocenyl]ethyl alcohol, 2,2'-bis(diphenylphosphino)-1,1'-dicyclopentane, sodium 2,2'-bis(diphenylphosphino)-1,1-binaphthyl-5,5'-disulfonate, sodium 2,2'-bis(di(3,5-xylyl)phosphino)-1,1-binaphthyl-5,5'-disulfonate, 1,1-(2,2'-bis(diphenylphosphino)-1,1'-binaphthyl-6,6'-diyl) bis(methylene)guanidine, 1,1-(2,2'-bis(di(3,5-xylyl)phosphino)-1,1'-binaphthyl-6,6'-diyl)bis(methylene)guanidine, (6,6'-bis(tris(3,3,4,4,5,5,6,6,7,7,8,8,8-tridecafluorooctyl)silyl)-1,1'-binaphthyl-2,2'-diyl)bis(diphenylphosphine), (6,6'-bis(tris(3,3,4,4,5,5,6,6,7,7,8,8,8-tridecafluorooctyl)silyl)-1,1'-binaphthyl-2,2'-diyl)bis(di(3,5-xylyl)phosphine), (2,2'-bis(diphenylphosphino)-1,1'-binaphthyl-4,4'-diyl)dimethanamine.hydrogen bromide salt, (2,2'-bis(di(3,5-xylyl)phosphino)-1,1'-binaphthyl-4,4'-diyl)dimethanamine.hydrogen bromide salt, (4,4'-bis(trimethylsilyl)-1,1'-binaphthyl-2,2'-diyl)bis(diphenylphosphine), (4,4'-bis(trimethylsilyl)-1,1'-binaphthyl-2,2'-diyl)bis(di(3,5-xylyl)phosphine), (4,4'-bis(triisopropylsilyl)-1,1'-binaphthyl-2,2'-diyl)bis(diphenylphosphine), (4,4'-bis(triisopropylsilyl)-1,1'-binaphthyl-2,2'-diyl)bis(di(3,5-xylyl)phosphine), 2,2'-bis(diphenylphosphino)-1,1'-binaphthyl-4,4'-diyldiphosphonic acid, 2,2'-bis(di(3,5-xylyl)phosphino)-1,1'-binaphthyl-4,4'-diyldiphosphonic acid, tetraethyl 2,2'-bis(diphenylphosphino)-1,1'-binaphthyl-4,4'-diyldiphosphonate, tetraethyl 2,2'-bis(di(3,5-xylyl)phosphino)-1,1'-binaphthyl-4,4'-diyldiphosphonate, (4,4'-diphenyl-1,1'-binaphthyl-2,2'-diyl)bis(diphenylphosphine), (4,4'-diphenyl-1,1'-binaphthyl-2,2'-diyl)bis(di(3,5-xylyl)phosphine), (4,4'-dichloro-1,1'-binaphthyl-2,2'-diyl)bis(diphenylphosphine), (4,4'-dichloro-1,1'-binaphthyl-2,2'-diyl)bis(di(3,5-xylyl)phosphine), (4,4'-dibromo-1,1'-binaphthyl-2,2'-diyl)bis(diphenylphosphine), (4,4'-dibromo-1,1'-binaphthyl-2,2'-diyl)bis(di(3,5-xylyl)phosphine), (4,4'-dimethyl-1,1'-binaphthyl-2,2'-diyl)bis(diphenylphosphine), (4,4'-dimethyl-1,1'-binaphthyl-2,2'-diyl)bis(di(3,5-xylyl)phosphine), (2,2'-bis(diphenylphosphino)-1,1'-binaphthyl-4,4'-diyl)bis(diphenylmethanol), (2,2'-bis(di(3,5-xylyl)phosphino)-1,1'-binaphthyl-4,4'-diyl)bis(diphenylmethanol), (4,4'-bis(1,1,1,2,2,3,3,4,4,5,5,6,6,8,8,9,9,10,10,11,11,12,12,13,13,13-hexacosafluoro-7-(perfluorohexyl)tridecan-7-yl)-1,1'-binaphthyl-2,2'-diyl)bis(diphenylphosphine), (4,4'-bis(1,1,1,2,2,3,3,4,4,5,5,6,6,8,8,9,9,10,10,11,11,12,12,13,13,13-hexacosafluoro-7-(perfluorohexyl)tridecan-7-yl)-1,1'-binaphthyl-2,2'-diyl)bis(di(3,5-xylyl)phosphine), (7,7'-dimethoxy-1,1'-binaphthyl-2,2'-diyl)bis(diphenylphosphine), (7,7'-dimethoxy-1,1'-binaphthyl-2,2'-diyl)bis(di(3,5-xylyl)phosphine), 4,4'-di-tert-butyl-4,4',5,5'-tetrahydro-3H,3'H-3,3'-bidinaphtho[2,1-c:1',2'-e]phosphapine, 1,2-bis(3H-dinaphtho[2,1-c:1',2'-e]phosphapin-4(5H)-yl)benzene, 3,3'-bis(diphenylphosphino)-4,4'-biphenanthrene, 3,3'-bis(di(3,5-xylyl)phosphino)-4,4'-biphenanthrene, (3,3'-diphenyl-1,1'-binaphthyl-2,2'-diyl)bis(methylene)bis(diphenylphosphine), (3,3'-diphenyl-1,1'-binaphthyl-2,2'-diyl)bis(methylene)bis(di(3,5-xylyl)phosphine), 2,2'-bis(diphenylphosphinooxy)-1,1'-binaphthyl, 2,2'-bis(di(3,5-xylyl)phosphinooxy)-1,1'-binaphthyl, (3,3'-dimethyl-1,1'-binaphthyl-2,2'-diyl)bis(oxy)bis(diphenylphosphine), (3,3'-dimethyl-1,1'-binaphthyl-2,2'-diyl)bis(oxy)bis(di(3,5-xylyl)phosphine), (3,3'-diphenyl-1,1'-binaphthyl-2,2'-diyl)bis(oxy)bis(diphenylphosphine), (3,3'-diphenyl-1,1'-binaphthyl-2,2'-diyl)bis(oxy)bis(di(3,5-xylyl)phosphine), (3,3'-bis(3,5-dimethylphenyl)-1,1'-binaphthyl-2,2'-diyl)bis(oxy)bis(diphenylphosphine), (3,3'-bis(3,5-dimethylphenyl)-1,1'-binaphthyl-2,2'-diyl)bis(oxy)bis(di(3,5-xylyl)phosphine), (3,3'-diphenyl-1,1'-binaphthyl-2,2'-diyl)bis(oxy)bis(bis(3,5-dimethylphenyl)phosphine), N2,N2'-bis(diphenylphosphino)-1,1'-binaphthyl-2,2'-diamine, N2,N2'-bis(di(3,5-xylyl)phosphino)-1,1'-binaphthyl-2,2'-diamine, (SP)-1-[(S)-α-(dimethylamino)-2-(diphenylphosphino)benzyl]-2-diphenylphosphinoferrocene, (RP)-1-[(R)-α-(dimethylamino)-2-(diphenylphosphino)benzyl]-2-diphenylphosphinoferrocene, (R)-1-{(RP)-2-[2-(diphenylphosphino)phenyl]ferrocenyl}ethyldiphenylphosphine, (S)-1-{(SP)-2-[2-(diphenylphosphino)phenyl]ferrocenyl}ethyldiphenylphosphine, (R)-1-{(RP)-2-[2-(diphenylphosphino)phenyl]ferrocenyl}ethyldicyclophosphine, (S)-1-{(SP)-2-[2-(diphenylphosphino)phenyl]ferrocenyl}ethyldicyclophosphine, (R)-1-{(RP)-2-[2-(diphenylphosphino)phenyl]ferrocenyl}ethyldi(2-norbonyl)phosphine, (S)-1-{SP)-2-[2-(diphenylphosphino)phenyl]ferrocenyl}ethyldi(2-norbonyl)phosphine, (R)-1-{(RP)-2-[2-(diphenylphosphino)phenyl]ferrocenyl}ethyldi(3,5-xylyl)phosphine, (S)-1-{(SP)-2-[2-(diphenylphosphino)phenyl]ferrocenyl}ethyldi(3,5-xylyl)phosphine, (R)-1-{(RP)-2-[2-[di(3,5-xylyl)phosphino]phenyl]ferrocenyl}ethyldi(3,5-xylyl)phosphine, (S)-1-{(SP)-2-[2-[di(3,5-xylyl)phosphino]phenyl]ferrocenyl}ethyldi(3,5-xylyl)phosphine, (R)-1-{(RP)-2-[2-(diphenylphosphino)phenyl]ferrocenyl}ethyl bis[3,5-bis-(trifluoromethyl)phenyl]phosphine, (S)-1-{(SP)-2-[2-(diphenylphosphino)phenyl]ferrocenyl}ethyl bis[3,5-bis-(trifluoromethyl)phenyl]phosphine, (R)-1-{(RP)-2-[2-[bis(4-methoxy-3,5-dimethylphenyl)phosphino]phenyl]ferrocenyl}ethylbis[3,5-bis(trifluoromethyl)phenyl]phosphine, (S)-1-{(SP)-2-[2-[bis(4-methoxy-3,5-dimethylphenyl)phosphino]phenyl]ferrocenyl}ethylbis[3,5-bis(trifluoromethyl)phenyl]phosphine, 3,3',4,4'-tetramethyl-1,1'-diphenyl-2,2',5,5'-tetrahydro-1H,1'H-2,2'-biphosphol, 1,1'-di-tert-butyl-2,2'-biphosphorane, 2,2'-di-tert-butyl-2,2',3,3'-tetrahydro-1H,1'H-1,1'-bisisophosphoindole, 1,2-bis(2,4-dimethylphosphoran-1-yl)ethane, 1,2-bis(2,5-dimethylphosphoran-1-yl)ethane, 1,2-bis(2,4-dimethylphosphetan-1-yl)benzene, 1,2-bis(2,5-dimethylphosphoran-1-yl)benzene, 3,4-bis(2,5-dimethylphosphoran-1-yl)furan-2,5-dione, 3,4-bis(2,5-diethylphosphoran-1-yl) furan-2,5-dione, 3,4-bis(2,5-dimethylphosphoran-1-yl)-1-phenyl-1H-pyrrole-2,5-dione, 1-(3,5-bis(trifluoromethyl)phenyl)-3,4-bis(2,5-dimethylphosphoran-1-yl)-1H-pyrrole-2,5-dione, 1-((1R,2S,4R,5S)-2,5-dimethyl-7-phosphabicyclo[2.2.1]heptan-7-yl)-2-((2R,5S)-2,5-dimethyl-7-phosphabicyclo[2.2.1]heptan-7-yl)benzene, 1,1'-(benzo[b]thiophene-2,3-diyl)bis(2,5-dimethylphosphorane), (2,2',4,4'-tetramethyl-3,3',4,4'-tetrahydro-2H,2'H-6,6'-bibenzo[b][1,4]dioxepin-7,7'-diyl)bis(diphenylphosphine), (2,2',4,4'-tetramethyl-3,3',4,4'-tetrahydro-2H,2'H-6,6'-bibenzo[b][1,4]dioxepin-7,7'-diyl)bis(di(3,5-xylyl)phosphine), ((6R)-6,7-dimethyl-6,7-dihydrodibenzo[e,g][1,4]dioxosin-1,12-diyl)bis(diphenylphosphine), ((6R)-6,7-dimethyl-6,7-dihydrodibenzo[e,g][1,4]dioxosin-1,12-diyl)bis(di(3,5-xylyl)phosphine), (4,4',5,5',6,6'-hexamethylbiphenyl-2,2'-diyl)bis(diphenylphosphine), (4,4',5,5',6,6'-hexamethylbiphenyl-2,2'-diyl)bis(di(3,5-xylyl)phosphine), (4,4',5,5',6,6'-hexamethoxybiphenyl-2,2'-diyl)bis(diphenylphosphine), (4,4',5,5',6,6'-hexamethoxybiphenyl-2,2'-diyl)bis(di(3,5-xylyl)phosphine), (5,5'-dichloro-4,4',6,6'-tetramethylbiphenyl-2,2'-diyl)bis(diphenylphosphine), (5,5'-dichloro-4,4',6,6'-tetramethylbiphenyl-2,2'-diyl)bis(di(3,5-xylyl)phosphine), (5,5'-dimethoxy-4,4',6,6'-tetramethylbiphenyl-2,2'-diyl)bis(diphenylphosphine), (5,5'-dimethoxy-4,4',6,6'-tetramethylbiphenyl-2,2'-diyl)bis(di(3,5-xylyl)phosphine), 2,2'-bis(diphenylphosphino)-6,6'-dimethoxybiphenyl-3,3'-diol, 2,2'-bis(di(3,5-xylyl)phosphino)-6,6'-dimethoxybiphenyl-3,3'-diol, (3,3',6,6'-tetramethoxybiphenyl-2,2'-diyl)bis(diphenylphosphine), (3,3',6,6'-tetramethoxybiphenyl-2,2'-diyl)bis(di(3,5-xylyl)phosphine), (3,3'-diisopropyl-6,6'-dimethoxybiphenyl-2,2'-diyl)bis(diphenylphosphine), (3,3'-diisopropyl-6,6'-dimethoxybiphenyl-2,2'-diyl)bis(di(3,5-xylyl)phosphine), (6,6'-dimethoxy-3,3'-bis(p-tolyloxy)biphenyl-2,2'-diyl)bis(diphenylphosphine), (6,6'-dimethoxy-3,3'-bis(p-tolyloxy)biphenyl-2,2'-diyl)bis(di(3,5-xylyl)phosphine), 2,2'-bis(diphenylphosphino)-6,6'-dimethoxybiphenyl-3,3'-diylbis(2,2-dimethylpropanoate), 2,2'-bis(di(3,5-xylyl)phosphino)-6,6'-dimethoxybiphenyl-3,3'-diylbis(2,2-dimethylpropanoate), (5,5'-dichloro-6,6'-dimethoxybiphenyl-2,2'-diyl)bis(diphenylphosphine), (5,5'-dichloro-6,6'-dimethoxybiphenyl-2,2'-diyl)bis(di(3,5-xylyl)phosphine), 6,6'-bis(diphenylphosphino)biphenyl-2,2'-diyl diacetate, 6,6'-bis(di(3,5-xylyl)phosphino)biphenyl-2,2'-diyl diacetate, 6,6'-bis(diphenylphosphino)biphenyl-2,2'-diylbis(2,2-dimethylpropanoate), 6,6'-bis(di(3,5-xylyl)phosphino)biphenyl-2,2'-diylbis(2,2-dimethylpropanoate), 6,6'-bis(diphenylphosphino)biphenyl-2,2'-diylbis(2-methylpropanoate), 6,6'-bis(di(3,5-xylyl)phosphino)biphenyl-2,2'-diylbis(2-methylpropanoate), 6,6'-bis(diphenylphosphino)biphenyl-2,2'-diyl dicyclohexane carboxylate, 6,6'-bis(di(3,5-xylyl)phosphino)biphenyl-2,2'-diyl dicyclohexane carboxylate, (4,4',6,6'-tetrakis(trifluoromethyl)biphenyl-2,2'-diyl)bis(diphenylphosphine), (4,4',6,6'-tetrakis(trifluoromethyl)biphenyl-2,2'-diyl)bis(di(3,5-xylyl)phosphine), (5-methoxy-4,6-dimethyl-4',6'-bis(trifluoromethyl)biphenyl-2,2'-diyl)bis(diphenylphosphine), (5-methoxy-4,6-dimethyl-4',6'-bis(trifluoromethyl)biphenyl-2,2'-diyl)bis(di(3,5-xylyl)phosphine), (2,2,2',2'-tetramethyl-4,4'-bibenzo[d][1,3]dioxol-5,5'-diyl)bis(diphenylphosphine), (2,2,2',2'-tetramethyl-4,4'-bibenzo[d][1,3]dioxol-5,5'-diyl)bis(di(3,5-xylyl)phosphine), 6,6'-bis(diphenylphosphino)-2,2',3,3'-tetrahydro-7,7'-bibenzofuran, 6,6'-bis(di(3,5-xylyl)phosphino)-2,2',3,3'-tetrahydro-7,7'- bibenzofuran, (2,2,2',2'-tetrafluoro-4,4'-bibenzo[d][1,3]dioxol-5,5'-diyl)bis(diphenylphosphine), (2,2,2',2'-tetrafluoro-4,4'-bibenzo[d][1,3]dioxol-5,5'-diyl)bis(di(3,5-xylyl)phosphine), 2-(naphthyl)-8-diphenylphosphino-1-[3,5-dioxa-4-phospha-cyclohepta[2,1-a;3,4-a']dinaphthalene-4-yl]-1,2-dihydroquinoline, 4,12-bis(di(3,5-xylyl)phosphino)-[2.2]-paracyclophane, 7,7'-bis(di(3,5-xylyl)phosphino)-2,2',3,3'-tetrahydro-1,1'-spirobiindane (Xyl-SDP), 7,7'-bis(diphenylphosphino)-2,2',3,3'-tetrahydro-1,1'-spirobiindane (SDP), bis(2-diphenylphosphinophenyl)ether (DPEphos), 4,5-bis(diphenylphosphinomethyl)-2,2-dimethyl-1,3-dioxolan (DIOP), 1,2-bis(diphenylphosphino)propane (PROPHOS), 2,3-bis(diphenylphosphino)butane (CHIRAPHOS), 1,2-bis[(2-methoxyphenyl)(phenyl)phosphino]ethane (DIPAMP), 3,4-bis(diphenylphosphino)-1-benzylpyrrolidine (DEGUPHOS), 2,3-bis(diphenylphosphino)-bicyclo[2.2.1]hepto-5-ene (NORPHOS), 1-tertiary-butoxycarbonyl-4-diphenylphosphino-2-(diphenylphosphinomethyl)pyrrolidine (BPPM), (2,2'-bis-(dibenzofuran-3,3-diyl)-bisdiphenylphosphine (BIBFUP), 2,2-bis(diphenylphosphino)-3,3-binaphtho[b]furan (BINAPFu), 2,2'-bis(diphenylphosphino)-3,3'-bi[benzo[b]thiophene] (BITIANP), N,N'-dimethyl-7,7'-bis(di(3,5-xylylyl)phosphino)-3,3',4,4'-tetrahydro-8,8'-bi-2H-1,4-benzoxazine (Xyl-Solphos), 2,3-bis(tertiary-butylmethylphosphino) quinoxaline (QuinoxP*), 2,4-bis(diphenylphosphino)pentane (SKEWPHOS), 2,4-bis(di(3,5-xylyl)phosphino)pentane (XylSKEWPHOS), 4,4'-bis(diphenylphosphino)-2,2',5,5'-tetramethyl-3,3'-bithiophene (TMBTP), 3,3'-bis(diphenylphosphonyl)-1,1'-2,2'-biindole (N-Me-2-BINPO), (2,2',5,5'-tetramethyl-3,3'-bithiophene-4,4'-diyl)bis(diphenylphosphine) (BITIANP), (4,4',6,6'-tetramethyl-3,3'-bibenzo[b]thiophene-2,2'-diyl)bis(diphenylphosphine) (tetraMe-BITIANP), 1,1'-bis(diphenylphosphino)-3,3'-dimethyl-1H,1'H-2,2'-biindole (BISCAP), 2,2'-bis(diphenylphosphino)-3,3'-bibenzofuran (BICUMP) and 2,2'-bis(diphenylphosphino)-1,1'-bibenzo[d]imidazole (BIMIP).

The diphosphine which can be used for the invention as specifically exemplified in the above may be an optically active diphosphine.

Next, a method for preparing the ruthenium complex of the invention will be explained.

The ruthenium complex of the invention can be prepared by the ruthenium compound represented as the Formula (A) reacting with a diamine compound, then to react with a metal salt having counter anion Y⁻, according to the following Scheme (10). Otherwise, the ruthenium complex of the invention can be prepared by the ruthenium compound represented as the Formula (B) reacting with a diphosphine compound represented by

P⌒P, and then with the diamine compound, further to react with a metal salt having counter anion Y⁻, according to the following Scheme (11). The ruthenium complex of the invention can be prepared by reacting with a metal salt having a counter anion Y⁻ with or without isolation of the ruthenium complex (9), the preferable method is the isolation method.

The ruthenium compound represented as the Formula (B) (hereinafter, referred to as an arene complex) is the commercial product, or can be prepared according to a known method. Otherwise, the ruthenium compound represented as the Formula (A) (hereinafter, referred to as an arene-phosphine complex) is the commercial product, or can be prepared by the arene complex represented as the Formula (B) reacting with a diphosphine compound represented by

P⌒P, according to a known method.

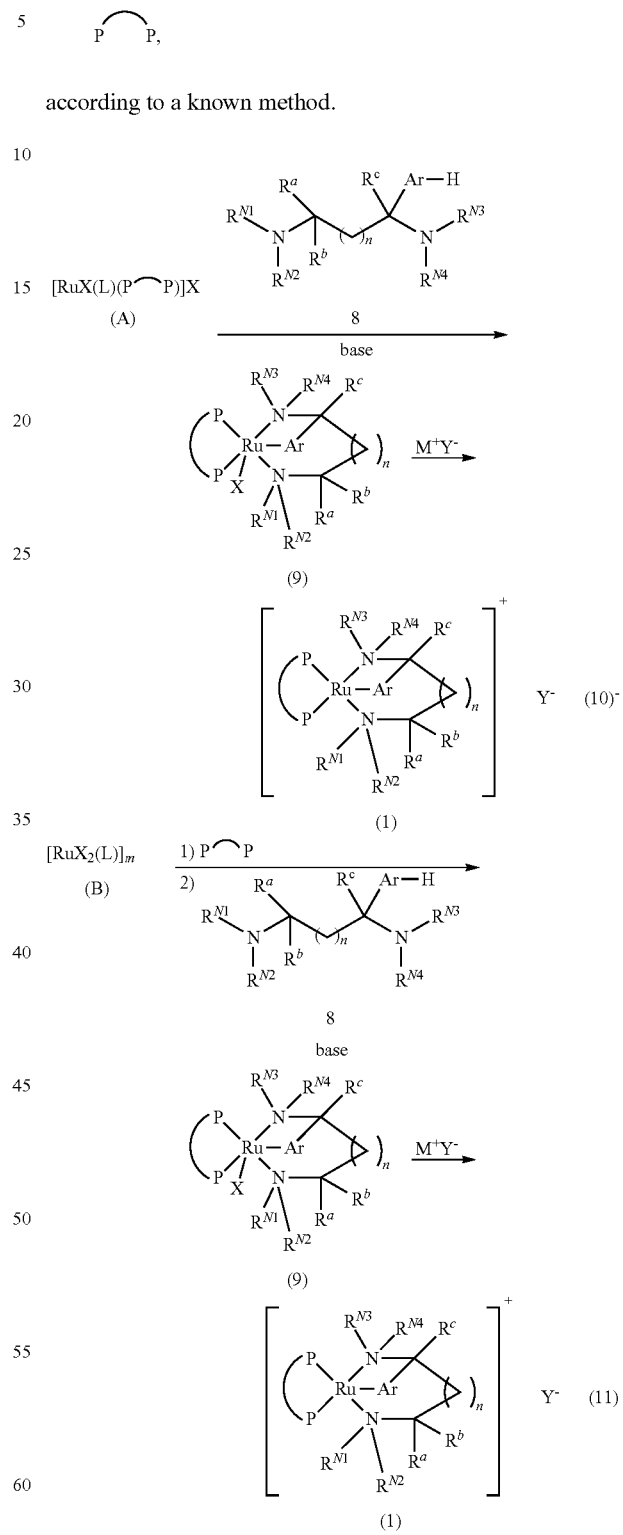

(M+, M+Y− in the Scheme (10) and (11), represent an alkali metal or a (primary, secondary or tertiary) ammonium.)

The examples of the arene represented as L in the Formula (A) or the Formula (B) include a $C_6$-$C_{20}$ aromatic compound which can coordinate to a ruthenium metal, preferably cyclic aromatic compound. The example of the preferably arene includes a benzene; an o-, m- or p-xylene; o-, m- or p-cymene; trimethyl benzene such as mesitylene. The preferable examples of the ruthenium compound represented as the Formula (B) include the ruthenium compound coordinating with an aromatic compound such as [RuCl$_2$(benzene)]$_2$, [RuCl$_2$(p-cymene)]$_2$ and [RuCl$_2$(mesitylene)]$_2$. Otherwise, the preferable example of the ruthenium compound represented as the Formula (A) include the ruthenium compound coordinating with a aromatic compound such as

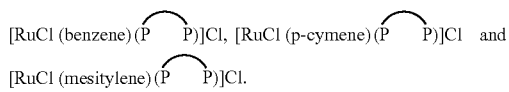

The examples of the diamine compound include the diamine compound having two endmost amino group that more than one of the amino groups have an α-substituent of aryl group, the preferably diamine compound represented by the following Formula (8)

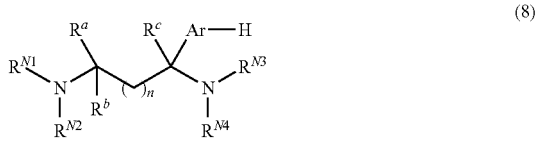

(8)

(in the formula, $R^a$, $R^b$ and $R^c$ each independently represent a hydrogen atom, an optionally substituted $C_1$-$C_{20}$ alkyl group, or an optionally substituted $C_2$-$C_{20}$ alkenyl group, an optionally substituted $C_3$-$C_8$ cycloalkyl group, an optionally substituted $C_7$-$C_{20}$ aralkyl group, an optionally substituted aryl group, or an optionally substituted heterocyclic group, or $R^b$ and $R^c$ may be form an alkylene group or an alkylenedioxy group; $R^{N1}$, $R^{N2}$, $R^{N3}$ and $R^{N4}$ each independently represent a hydrogen atom, an optionally substituted $C_1$-$C_{20}$ alkyl group, an optionally substituted $C_2$-$C_{20}$ alkenyl group, an optionally substituted $C_7$-$C_{20}$ aralkyl group, or an optionally substituted $C_3$-$C_8$ cycloalkyl group, and at least one of $R^{N1}$, $R^{N2}$, $R^{N3}$ and $R^{N4}$ represents a hydrogen atom; or $R^{N1}$ and $R^a$ may form an alkylene group, and n is an integer of 0 to 3 and Ar represents an optionally substituted arylene group.)

Meanings of the each symbol of the substituent group included in the Formula (8) are the same as those described above.

Specific examples of the diamine compound represented by the Formula (8) used in the invention include 1,2-diphenylethylenediamine, 1,2-bis(4-methoxyphenyl)ethylenediamine, 1-methyl-2,2-diphenylethylenediamine, 1-isobutyl-2,2-diphenylethylenediamine, 1-isopropyl-2,2-diphenylethylenediamine (DPIPEN), 1-methyl-2,2-bis(4-methoxyphenyl)ethylenediamine (DAMEN), 1-isobutyl-2,2-bis(4-methoxyphenyl)ethylenediamine, 1-isopropyl-2,2-bis(4-methoxyphenyl)ethylenediamine (DAIPEN), 1-phenyl-2,2-bis(4-methoxyphenyl)ethylenediamine, 1,1-diphenylethylenediamine (1,1-DPEN), 1,1-bis(4-methoxyphenyl)ethylenediamine (DAEN) and 1-isopropyl-2,2-bis(3-methoxyphenyl)ethylenediamine (3-DAIPEN). These diamine compounds may be an optically active diamine compound. In the case of an optically active diamine compound, there is (R) or (S) at the ahead of its name to show the optically activity.

Specifically, the method for preparing the ruthenium complex of the invention is as follows.

The method for preparing an arene-phosphine complex is described, see e.g. J. CHEM. SOC., CHEM. COMMUN 1208 (1989), and by reacting the arene-phosphine complex present as the prepared solution or as a solid matter obtained after crystallization, and solvent drying, etc. with the diamine compound represented by the Formula (8) in an amount of at least one equivalent, preferably 1 to 20 equivalents, more preferably 1 to 10 equivalents, and still more preferably 1.1 to 5 equivalents relative to the arene-phosphine complex, the ruthenium complex of the invention can be obtained. In addition, the preparation method of the invention is carried out in the presence of an alcohol, and the alcohol may be used singly or in combination with other solvents. Examples of the alcohol used herein include a lower alkanol such as methanol, ethanol, n-propanol, 2-propanol and n-butanol. Preferred examples of alcohol include methanol and ethanol. In addition, although an additive is not necessarily required, by adding 0.1 to 2 equivalents, preferably 0.5 to 1.5 equivalents and more preferably 0.9 to 1.1 equivalents of a base relative to the arene-phosphine complex, the complex can be efficiently produced.

As a base, an inorganic base and an organic base can be mentioned. Examples of an inorganic base include potassium carbonate ($K_2CO_3$), lithium hydroxide (LiOH), sodium hydrogen carbonate ($NaHCO_3$), sodium carbonate ($Na_2CO_3$), potassium hydrogen carbonate ($KHCO_3$), potassium methoxide ($KOCH_3$), sodium methoxide ($NaOCH_3$), lithium methoxide ($LiOCH_3$), sodium ethoxide ($NaOCH_2CH_3$), sodium acetate ($CH_3CO_2Na$), potassium isopropoxide ($KOCH(CH_3)_2$), potassium tert-butoxide ($KOC(CH_3)_3$), potassium naphthalenide ($KC_{10}H_8$), cesium carbonate ($Cs_2CO_3$) and silver carbonate ($Ag_2CO_3$). Examples of an organic base include an organic amines such as triethylamine, diethylamine, diisopropylamine, diisopropylethylamine, N,N-dimethylaniline, piperidine, pyridine, 4-dimethylaminopyridine, 1,5-diazabicyclo[4.3.0]nona-5-ene, 1,8-diazabicyclo[5.4.0]undeca-7-ene, tri-n-butylamine and N-methylmorpholine.

The ruthenium complex of the invention can be obtained by reacting a compound having a counter anion in amount of at least one equivalent, preferably 1 to 20 equivalents, more preferably 1 to 10 equivalents, and still more preferably 1.0 to 5 equivalents relative to the ruthenium complex represented by the Formula (A), (B) or (9) with the ruthenium complex (9) prepared in situ or isolation method. In addition, the above preparation method can be carried out in the presence of an organic solvent. The organic solvent can be used singly or in combination with other organic solvents. Examples of the alcohol used herein include toluene, benzene, dichloromethane, chloroform, THF, dioxane, hexane, heptane, DMF, ethyl acetate, butyl acetate, acetonitrile, methanol, ethanol, isopropyl alcohol and butanol. Preferred solvent is dichloromethane. The present invention affords the method of manufacturing the ruthenium complex represented by the Formula (1), which is the ruthenium complex represented by the Formula (9), prepared in situ or isolation, is reacted with the metal salt having the counter anion $Y^-$ in the presence of an organic solvent.

As a catalyst for an asymmetric reduction, the ruthenium complex of the invention has an excellent catalytic activity. By using the ruthenium complex of the invention as a catalyst for an asymmetric reduction, alcohols can be produced by an asymmetric reduction of a carbonyl group. Examples of the carbonyl group for the preparation method of the invention include a carbon/oxygen double bond such as a keto group and an ester group. Preferable carbonyl group includes a keto group. In particular, as being in excellent in terms of enantioselectivity, etc., the catalyst for an asymmetric reduction of the invention is suitable for a method for producing optically active alcohols from a prochiral keto groups.

The method for preparing alcohols of the invention can be preferably carried out with or without a solvent. However, it is preferably carried out by in the presence of a solvent. As for the solvent used, those which can dissolve a substrate and a catalyst are preferable, and a single solvent or a mixture solvent is used. Specific examples include an aromatic hydrocarbon such as toluene and xylene, an aliphatic hydrocarbon such as hexane and heptane, a halogenated hydrocarbon such as methylene chloride and chlorobenzene, an ether such as diethyl ether, tetrahydrofuran, methyl tert-butyl ether and cyclopentylmethyl ether, an alcohol such as methanol, ethanol, 2-propanol, n-butyl alcohol, 2-butanol and tert-butyl alcohol, and a polyol such as ethylene glycol, propylene glycol, 1,2-propanediol and glycerin. Among these, an ether or an alcohol is preferable. Particularly preferred solvents include tetrahydrofuran (THF), methanol, ethanol and 2-propanol. Use amount of the solvent can be appropriately selected depending on the reaction condition, etc. The reaction is carried out under stirring, if necessary.

The use amount of the catalyst varies with the reduced substrate, a reaction condition or type of a catalyst, etc., but it is generally in the range of 0.00001 mol % to 1 mol %, and preferably 0.0001 mol % to 0.5 mol % in terms of the molar ratio of the ruthenium metal relative to the substrate to be reduced.

Moreover, the asymmetric reduction of the invention is preferably carried out by adding base compounds. Examples of the base compound to be used include an inorganic base and an organic base. Examples of the inorganic base include potassium carbonate ($K_2CO_3$), potassium hydroxide (KOH), lithium hydroxide (LiOH), sodium hydrogen carbonate ($NaHCO_3$), sodium carbonate ($Na_2CO_3$), potassium hydrogen carbonate ($KHCO_3$) and sodium hydroxide (NaOH). Examples of the organic base include an alkali or an alkali-earth metal salt such as potassium methoxide ($KOCH_3$), sodium methoxide ($NaOCH_3$), lithium methoxide ($LiOCH_3$), sodium ethoxide ($NaOCH_2CH_3$), potassium isopropoxide ($KOCH(CH_3)_2$), potassium tert-butoxide ($KOC(CH_3)_3$), and potassium naphthalenide ($KC_{10}H_8$) and an organic amine such as triethylamine, diethylamine, diisopropylethylamine, N,N-dimethylaniline, piperidine, pyridine, 4-dimethylaminopyridine, 1,5-diazabicyclo[4.3.0]nona-5-ene, 1,8-diazabicyclo[5.4.0]undeca-7-ene, tri-n-butylamine and N-methylmorpholine. In addition, the base to be used in the invention can be metal hydrides such as sodium hydride and potassium hydride. In addition, the base to be used in the invention is not limited to the bases described above, and a hydrogen and others that can generate an amine-phosphine ruthenium hydride complex can be used. These bases can be used singly or in appropriate combination of two or more. Preferred examples of the base compound include an inorganic base and an alkali or an alkali-earth metal salt.

The use amount of the base compound is 1 to 10000 equivalents, and preferably 10 to 5000 equivalents compared to the mole number of the ruthenium complex, or it is in the range of 0.00001 mol % to 50 mol %, and preferably 0.0001 mol % to 30 mol % in terms of the molar ratio of the base compound relative to the substrate to be reduced.

With regard to the method of the invention, the reaction temperature for carrying out an asymmetric hydrogenation as an asymmetric reduction is −30° C. to 100° C., and preferably 0° C. to 50° C. If the reaction temperature is too low, large amount of the raw materials may remain unreacted. On the other hand, if it is too high, the raw materials and the catalyst may decompose, and therefore undesirable. The present invention is also characterized in that the asymmetric hydrogenation can be carried out at low temperature, for example −30 to 30° C.

With regard to the invention, as the catalytic system has an extremely high activity, the hydrogen pressure as atmospheric pressure (0.1 MPa) which is enough for carrying out the asymmetric hydrogenation. However, it is preferably 0.1 MPa to 10 MPa, more preferably 0.1 MPa to 6 MPa, and still more preferably 0.1 MPa to 3 MPa. Furthermore, the reaction time is 1 minute to 72 hours, and preferably 30 minutes to 98 hours to obtain sufficiently high conversion rate of the raw materials.

With regard to the asymmetric reduction of the invention, an asymmetric hydrogen-transfer reduction is carried out by reacting the ruthenium complex of the invention in the presence of a hydrogen donor. The hydrogen donor is not specifically limited if it was generally used for an asymmetric hydrogen-transfer reduction, including formic acid or its salt, and an alcohol in which a hydrogen atom is present at a position of the carbon atom substituted with a hydroxy group, i.e., 2-propanol. However, combination of 2-propanol and a base compound is preferable. The examples of the base which can be used herein include a tertiary organic amines such as trimethylamine, triethylamine and triisopropylamine, and an inorganic base such as LiOH, NaOH, KOH and $K_2CO_3$. The base is used in an excess amount compared to the ruthenium complex, for example, 1 to 10,000 times in molar ratio.

If the hydrogen donor is a liquid, it can be generally used as a solvent for the reaction. However, it is also possible to use a non-hydrogen donor solvent such as toluene, tetrahydrofuran, acetonitrile, dimethyl formamide (DMF) and dimethyl sulfoxide (DMSO) as a co-solvent, either singly or as a mixture for dissolving the raw materials.

The use amount of the ruthenium complex as a catalyst is generally selected within the range of 0.000001 mol % to 5 mol %, and preferably 0.0001 mol % to 2 mol % in terms of molar ratio of the ruthenium complex compared to the substrate to be reduced.

The use amount of the hydrogen donor compared to the substrate to be reduced is generally the same molar amount or more, and when the hydrogen donor is formic acid or its salt, it is preferably used within the range of 1.5 times molar amounts or more, and also 20 times molar amounts or less, and preferably 10 times molar amounts or less. On the other hand, when the hydrogen donor is 2-propanol or the like, the hydrogen donor is used in a large excess with respect to the substrate from the viewpoint of reaction equilibrium, and is usually used in a 1000-fold molar amount or less.

The reaction temperature is selected within the range of −70 to 100° C., and preferably 0 to 70° C.

The reaction pressure is not specifically limited, and it is generally 0.05 to 0.2 MPa, preferably atmospheric pressure.

The reaction time is 0.5 to 100 hours, and generally 1 to 50 hours.

After the reaction is completed, a purification method which is generally used, for example, an extraction, a filtration, a crystallization, a distillation and various chromatographies, is carried out either singly or in appropriate combination to obtain desired alcohols.

EXAMPLES

Hereinafter, the Examples are described and the invention will be described in greater detail. However, the invention is not limited by the following Examples.

Measurement of $^1$H-NMR spectrum and $^{31}$P-NMR spectrum was carried out by using MERCURY plus 300 manufactured by Varian Inc.

Example 1

(1) Preparation of RuCl[(S)-daipena][(S)-xylbinap]

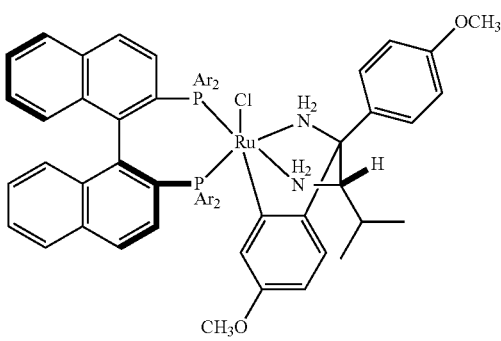

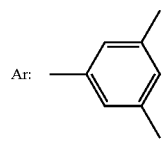

Under a nitrogen gas, [RuCl$_2$(p-cymene)]$_2$ 3.07 g (5.0 mmol), (S)-XylBINAP 7.35 g (10.0 mmol) and methanol 110 mL were added to a 200 mL 4-neck flask. The mixture was heated to 50° C. and stirred for 2 hours to prepare [RuCl(p-cymene)((S)-xylbinap)]Cl. The reaction solution was cooling down to room temperature, then diethylamine 736 mg (10 mmol) and (S)-DAIPEN 3.48 g (11.1 mmol) were added to the reaction solution, and stirred for 3 hours at 60° C. After concentration, the residue was dissolved in butyl acetate and the precipitated salts were separated by filtration. The filtrate was concentrated and the mixture added with heptane (110 mL) was cooling down to −10° C. The precipitated crystals were filtered to obtain the title compound (11.62 g) with yield of 98%.

$^{31}$P-NMR (C$_6$D$_6$): δ
53.2 (d, J=38.6 Hz), 61.0 (d, J=38.6 Hz)

(2) Preparation of {Ru[(S)-daipena][(S)-xylbinap]}BF$_4$

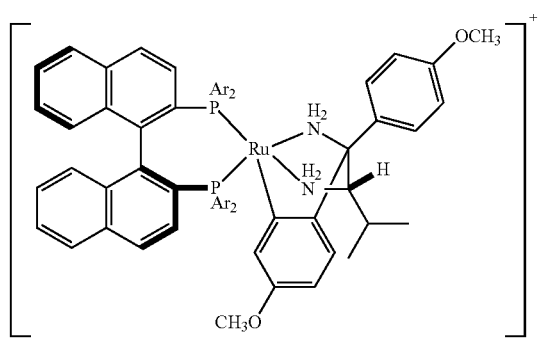

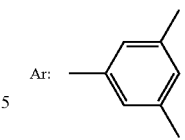

Under a nitrogen gas, RuCl[(S)-daipena][(S)-xylbinap] 154 mg (0.13 mmol), AgBF$_4$ 25.3 mg (0.13 mmol) and dichloromethane 6 ml were added to the 100 ml Schlenk tube, and stirred at room temperature for 2 hours. The precipitated salt was filtered out from the reaction solution. The filtrate was concentrated and dried in vacuo to obtain the title compound 153 mg, 95% yield.

$^{31}$P-NMR (CD$_3$OD): δ
19.6 (d, J=53.9 Hz), 36.6 (d, J=53.7 Hz)

Example 2

Preparation of {Ru[(S)-daipena][(S)-xylbinap]}PF$_6$

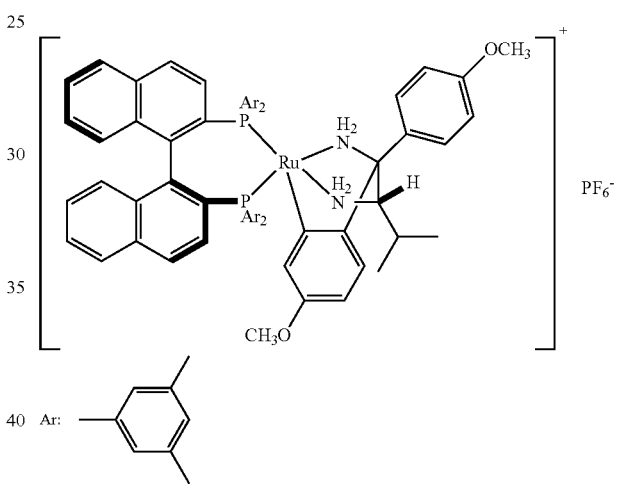

Under a nitrogen gas, RuCl [(S)-daipena][(S)-xylbinap] 154 mg (0.13 mmol), AgPF$_6$ 32.9 mg (0.13 mmol) and dichloromethane 6 ml were added to the 100 ml Schlenk tube, and stirred at room temperature for 2 hours. The precipitated salt was filtered out from the reaction solution. The filtrate was concentrated and dried in vacuo to obtain the title compound 168 mg, 97% yield.

$^{31}$P-NMR (CD$_3$OD): δ
19.6 (d, J=53.9 Hz), 36.6 (d, J=53.7 Hz)

Comparative Example 1

Preparation of (R)-1-phenylethanol

To a 100 mL autoclave with a stirrer bar, acetophenone (1.2 g, 10 mmol) and {RuCl[(S)-daipena][(S)-xylbinap]}PF$_6$ (the complex described in the Patent Literature 4) (13.3 mg, 0.01 mmol, 1/1000 molar fold of acetophenone) were added. After purging with a nitrogen gas, toluene (5 mL) and 1,8-diazabicyclo[5,4,0]undeca-7-ene (15.2 mg, 0.1 mmol) were added thereto. Subsequently, purging with a hydrogen gas, the mixture was stirred at 30° C. for 3 hours under hydrogen pressure 1 MPa. As a result of analysis of the reaction mixture by gas chromatography (Chirasil-DEX CB), it was found that the conversion rate is 1.4%.

Example 3

Preparation of (R)-1-phenylethanol

To a 100 mL autoclave with a stirrer bar, acetophenone (1.2 g, 10 mmol) and {Ru[(S)-daipena][(S)-xylbinap]}BF$_4$ obtained from Example 1 above (12.4 mg, 0.01 mmol, 1/1000 molar fold of acetophenone) were added. After purging with a nitrogen gas, toluene (5 mL) and 1,8-diazabicyclo[5,4,0]undeca-7-ene (15.2 mg, 0.1 mmol) were added thereto. Subsequently, purging with a hydrogen gas, the mixture was stirred at 30° C. for 3 hours under hydrogen pressure 1 MPa. As a result of analysis of the reaction mixture by gas chromatography (Chirasil-DEX CB), it was found that the conversion rate is 95.4% and optical purity is 98.5% ee.

Example 4

Preparation of (R)-1-phenylethanol

To a 100 mL autoclave with a stirrer bar, acetophenone (1.2 g, 10 mmol) and {Ru[(S)-daipena][(S)-xylbinap]}PF$_6$ obtained from Example 2 above (12.9 mg, 0.01 mmol, 1/1000 molar fold of acetophenone) were added. After purging with a nitrogen gas, toluene (5 mL) and 1,8-diazabicyclo[5,4,0]undeca-7-ene (15.2 mg, 0.1 mmol) were added thereto. Subsequently, purging with a hydrogen gas, the mixture was stirred at 30° C. for 3 hours under hydrogen pressure 1 MPa. As a result of analysis of the reaction mixture by gas chromatography (Chirasil-DEX CB), it was found that the conversion rate is 99.6% and optical purity is 99.6% ee.

When Example 3 and Example 4 are compared to Comparative example 1, it was found that the catalytic activity of Comparative example 1 is very low, however the conversion rate of the Examples 3 and 4 show over 95%.

The invention claimed is:

1. A ruthenium complex having the following Formula (2)

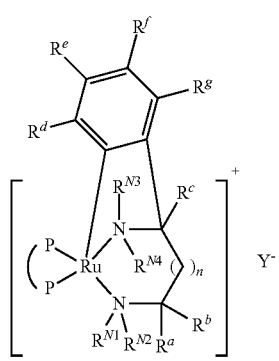

(2)

(wherein, P∩P represents a diphosphine; Y⁻ represents a counter anion; $R^a$, $R^b$, and $R^c$ each independently represent a hydrogen atom, an optionally substituted $C_1$-$C_{20}$ alkyl group, an optionally substituted $C_2$-$C_{20}$ alkenyl group, an optionally substituted $C_3$-$C_8$ cycloalkyl group, an optionally substituted $C_7$-$C_{20}$ aralkyl group, an optionally substituted aryl group or an optionally substituted heterocyclic group, and $R^b$ and $R^c$ may form an alkylene group or an alkylenedioxy group; $R^d$, $R^e$, $R^f$ and $R^g$ each independently represent a hydrogen atom, an alkyl group having 1 to 20 carbon atoms, a halogenated alkyl group having 1 to 5 carbon atoms, a halogen atom, an optionally substituted aryl group, an optionally substituted $C_3$-$C_8$ cycloalkyl group, a tri-substituted silyl group or an alkoxy group having 1 to 20 carbon atoms; $R^{N1}$, $R^{N2}$, $R^{N3}$ and $R^{N4}$ each independently represent a hydrogen atom, an optionally substituted $C_1$-$C_{20}$ alkyl group, an optionally substituted $C_2$-$C_{20}$ alkenyl group, an optionally substituted $C_7$-$C_{20}$ aralkyl group or an optionally substituted $C_3$-$C_8$ cycloalkyl group, and at least one of $R^{N1}$, $R^{N2}$, $R^{N3}$ and $R^{N4}$ represents a hydrogen atom; and $R^{N1}$ and $R^a$ may form an alkylene group).

2. The ruthenium complex according to claim 1, wherein the ruthenium complex is having the following Formula (3)

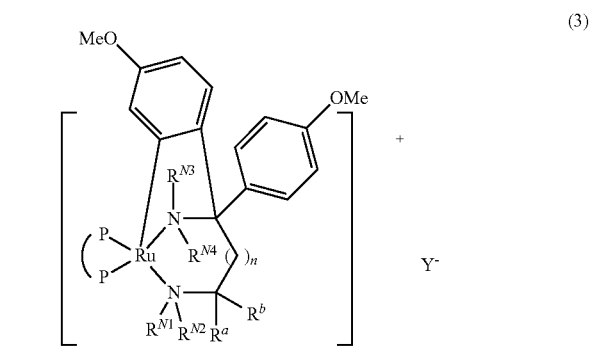

(3)

(wherein, P∩P represents a diphosphine; Y⁻ represents a counter anion; $R^a$ and $R^b$ each independently represent a hydrogen atom, an optionally substituted $C_1$-$C_{20}$ alkyl group, an optionally substituted $C_2$-$C_{20}$ alkenyl group, an optionally substituted $C_3$-$C_8$ cycloalkyl group, an optionally substituted $C_7$-$C_{20}$ aralkyl group, an optionally substituted aryl group or an optionally substituted heterocyclic group; $R^{N1}$, $R^{N2}$, $R^{N3}$ and $R^{N4}$ each independently represent a hydrogen atom, an optionally substituted $C_1$-$C_{20}$ alkyl group, an optionally substituted $C_2$-$C_{20}$ alkenyl group, an optionally substituted $C_7$-$C_{20}$ aralkyl group or an optionally substituted $C_3$-$C_8$ cycloalkyl group, and at least one of $R^{N1}$, $R^{N2}$, $R^{N3}$ and $R^{N4}$ represents a hydrogen atom; and $R^{N1}$ and $R^a$ may form an alkylene group).

3. The ruthenium complex according to claim 1, wherein the diphosphine indicated as P∩P is a diphosphine having the following Formula (4)

$R^1R^2P-Q-PR^3R^4$ (4)

(wherein, $R^1$, $R^2$, $R^3$ and $R^4$ each independently represent an optionally substituted aryl group, an optionally substituted cycloalkyl group or an optionally substituted alkyl group, and $R^1$ and $R^2$ and/or $R^3$ and $R^4$ may form a ring; and Q represents an optionally substituted divalent arylene group, a biphenyldiyl group, a binaphthalenediyl group, a bipyridinediyl group, a paracyclophanediyl group or a ferrocenediyl group).

4. The ruthenium complex according to claim 1, wherein the diphosphine indicated as P∩P is an optically active diphosphine.

5. The ruthenium complex according to claim 4, wherein the optically active diphosphine indicated as P∩P is a diphosphine having the following Formula (5)

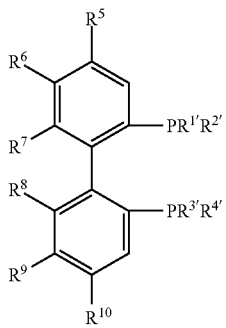

(5)

(wherein, $R^{1'}$, $R^{2'}$, $R^{3'}$ and $R^{4'}$ each independently represent a phenyl group, a cyclopentyl group or a cyclohexyl group, and any of which is optionally substituted with a substituent group selected from a group consisting of an alkyl group having 1 to 4 carbon atoms and an alkoxy group having 1 to 4 carbon atoms; $R^5$, $R^6$, $R^7$, $R^8$, $R^9$ and $R^{10}$ each independently represent a hydrogen atom, an alkyl group having 1 to 4 carbon atoms, an alkoxy group having 1 to 4 carbon atoms, a halogen atom, a halogenated alkyl group or an dialkylamino group having 1 to 4 carbon atoms, and two of $R^5$, $R^6$ and $R^7$ may form an optionally substituted alkylene group; an optionally substituted alkylenedioxy group; or an optionally substituted aromatic ring, two of $R^8$, $R^9$ and $R^{10}$ may form an optionally substituted alkylene group; an optionally substituted alkylenedioxy group; or an optionally substituted aromatic ring; and $R^7$ and $R^8$ may form an optionally substituted alkylene group; an optionally substituted alkylenedioxy group; or an optionally substituted aromatic ring, with the proviso that any of $R^7$ and $R^8$ is not a hydrogen atom).

6. The ruthenium complex according to claim 5, wherein $R^{1'}$, $R^{2'}$, $R^{3'}$ and $R^{4'}$ in the Formula (5) is a 3,5-xylyl group.

7. An asymmetric reduction catalyst comprising the ruthenium complex according to claim 4.

8. An asymmetric reduction catalyst comprising the ruthenium complex according to claim 5.

9. An asymmetric reduction catalyst comprising the ruthenium complex according to claim 6.

10. The ruthenium complex according to claim 2, wherein the diphosphine indicated as P∩P is a diphosphine having the following Formula(4)

$$R^1R^2P\text{-}Q\text{-}PR^3R^4 \qquad (4)$$

(wherein, $R^1$, $R^2$, $R^3$ and $R^4$ each independently represent an optionally substituted aryl group, an optionally substituted cycloalkyl group or an optionally substituted alkyl group, and $R^1$ and $R^2$ and/or $R^3$ and $R^4$ may form a ring; and Q represents an optionally substituted divalent arylene group, a biphenyldiyl group, a binaphthalenediyl group, a bipyridinediyl group, a paracyclophanediyl group or a ferrocenediyl group).

11. The ruthenium complex according to claim 10, wherein the diphosphine indicated as P∩P is an optically active diphosphine.

12. The ruthenium complex according to claim 11, wherein the optically active diphosphine indicated as P∩P is a diphosphine having the following Formula (5)

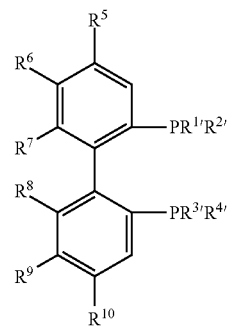

(5)

(wherein, $R^{1'}$, $R^{2'}$, $R^{3'}$ and $R^{4'}$ each independently represent a phenyl group, a cyclopentyl group or a cyclohexyl group, and any of which is optionally substituted with a substituent group selected from a group consisting of an alkyl group having 1 to 4 carbon atoms and an alkoxy group having 1 to 4 carbon atoms; $R^5$, $R^6$, $R^7$, $R^8$, $R^9$ and $R^{10}$ each independently represent a hydrogen atom, an alkyl group having 1 to 4 carbon atoms, an alkoxy group having 1 to 4 carbon atoms, a halogen atom, a halogenated alkyl group or an dialkylamino group having 1 to 4 carbon atoms, and two of $R^5$, $R^6$ and $R^7$ may form an optionally substituted alkylene group; an optionally substituted alkylenedioxy group; or an optionally substituted aromatic ring, two of $R^8$, $R^9$ and $R^{10}$ may form an optionally substituted alkylene group; an optionally substituted alkylenedioxy group; or an optionally substituted aromatic ring; and $R^7$ and $R^8$ may form an optionally substituted alkylene group; an optionally substituted alkylenedioxy group; or an optionally substituted aromatic ring, with the proviso that any of $R^7$ and $R^8$ is not a hydrogen atom).

13. The ruthenium complex according to claim 12, wherein $R^{1'}$, $R^{2'}$, $R^{3'}$ and $R^{4'}$ in the Formula (5) is a 3,5-xylyl group.

14. An asymmetric reduction catalyst comprising the ruthenium complex according to claim 11.

15. An asymmetric reduction catalyst comprising the ruthenium complex according to claim 12.

16. An asymmetric reduction catalyst comprising the ruthenium complex according to claim 13.

* * * * *